(12) United States Patent
Tani

(10) Patent No.: US 11,595,621 B2
(45) Date of Patent: Feb. 28, 2023

(54) ENDOSCOPE APPARATUS, ENDOSCOPE, AND IMAGE GENERATION METHOD

(71) Applicant: OLYMPUS CORPORATION, Tokyo (JP)

(72) Inventor: Shinsuke Tani, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 18 days.

(21) Appl. No.: 17/082,544

(22) Filed: Oct. 28, 2020

(65) Prior Publication Data

US 2021/0105467 A1 Apr. 8, 2021

Related U.S. Application Data

(63) Continuation of application No. PCT/JP2019/007105, filed on Feb. 25, 2019.

(30) Foreign Application Priority Data

May 1, 2018 (JP) .............................. JP2018-088334

(51) Int. Cl.
*H04N 19/115* (2014.01)
*H04N 19/136* (2014.01)
(Continued)

(52) U.S. Cl.
CPC ......... *H04N 7/183* (2013.01); *A61B 1/00016* (2013.01); *A61B 1/00045* (2013.01);
(Continued)

(58) Field of Classification Search
CPC ............ A61B 1/00006; A61B 1/00009; A61B 1/00016; A61B 1/00045; A61B 1/045;
(Continued)

(56) References Cited

U.S. PATENT DOCUMENTS 6,427,025 B1 * 7/2002 Shimomura .............. G06T 9/00
375/E7.077
10,945,592 B2 * 3/2021 Takenouchi ........... A61B 1/045
(Continued)

FOREIGN PATENT DOCUMENTS

JP  2007-329946 A    12/2007
JP  2007329946 A  * 12/2007
(Continued)

OTHER PUBLICATIONS

International Search Report dated May 21, 2019 issued in PCT/JP2019/007105.

*Primary Examiner* — Christopher S Kelley
*Assistant Examiner* — Asmamaw G Tarko
(74) *Attorney, Agent, or Firm* — Scully, Scott, Murphy & Presser, P.C.

(57) ABSTRACT

An endoscope apparatus includes a compression processing control unit configured to carry out a compression processing of compressing image data by using a compression parameter to generate compressed data, a monitor that is a display unit configured to display a display image corresponding to the image data, an information quantity detection unit configured to detect a quantity of information on an object contained in the image data, and a judgement unit configured to carry out a judgement processing of judging whether or not a judgement value corresponding to the quantity of information is smaller than a predetermined threshold. The image pickup of the object and the generation of the image data are continuously performed multiple times, and the judgement processing is carried out whenever the image data is generated. The compression parameter and the display image are determined based on a result of the judgement processing.

14 Claims, 13 Drawing Sheets

(51) Int. Cl.
*H04N 19/146* (2014.01)
*A61B 1/00* (2006.01)
*A61B 1/045* (2006.01)
*A61B 1/05* (2006.01)
*H04N 7/18* (2006.01)
*H04N 5/225* (2006.01)

(52) U.S. Cl.
CPC ............. *A61B 1/045* (2013.01); *A61B 1/05* (2013.01); *H04N 5/225* (2013.01); *H04N 19/115* (2014.11); *H04N 19/136* (2014.11); *H04N 19/146* (2014.11); *A61B 1/00009* (2013.01); *H04N 2005/2255* (2013.01)

(58) Field of Classification Search
CPC ...... A61B 1/05; H04N 19/115; H04N 19/136; H04N 19/146; H04N 2005/2255; H04N 5/225; H04N 5/23203; H04N 7/183
USPC ............................................. 348/65
See application file for complete search history.

(56) References Cited

U.S. PATENT DOCUMENTS

| | | | |
|---|---|---|---|
| 2002/0102027 A1* | 8/2002 | Miyake | H04N 19/124 375/E7.231 |
| 2009/0180684 A1* | 7/2009 | Tani | G06K 9/00134 382/162 |
| 2010/0231736 A1* | 9/2010 | Hosokawa | H04N 19/115 348/222.1 |
| 2017/0311777 A1* | 11/2017 | Hirayama | A61B 1/00006 |
| 2018/0220873 A1* | 8/2018 | Tani | A61B 1/00036 |
| 2018/0365836 A1* | 12/2018 | Liao | G06T 7/143 |
| 2021/0105467 A1* | 4/2021 | Tani | A61B 1/045 |

FOREIGN PATENT DOCUMENTS

| | | | | |
|---|---|---|---|---|
| JP | 2016-87248 A | | 5/2016 | |
| JP | 2016-123825 A | | 7/2016 | |
| JP | 2016123825 A | * | 7/2016 | |
| JP | 6192882 B1 | | 9/2017 | |
| JP | 6253600 B2 | | 12/2017 | |
| WO | 2015-111292 A1 | | 7/2015 | |
| WO | WO-2017061495 A1 | * | 4/2017 | ......... A61B 1/00009 |

* cited by examiner

ENDOSCOPE APPARATUS, ENDOSCOPE, AND IMAGE GENERATION METHOD

CROSS REFERENCE TO RELATED APPLICATION

This application is a continuation application of PCT/JP2019/007105 filed on Feb. 25, 2019 and claims benefit of Japanese Application No. 2018-088334 filed in Japan on May 1, 2018, the entire contents of which are incorporated herein by this reference.

BACKGROUND OF THE INVENTION

1. Field of the Invention

The present invention relates to an endoscope apparatus including a compression processing control unit configured to compress image data and a display unit configured to display a display image corresponding to the image data, an endoscope, and an image generation method.

2. Description of the Related Art

In recent years, endoscopes have been widely used in medical and industrial fields. An endoscope used in the medical field, in particular, is widely used, for example, to observe organs in a body cavity, perform treatment using a treatment instrument, and perform a surgical operation under endoscopic observation.

Further, in recent years, progress in semiconductor technologies and electric power saving achieved by using an LED as an illumination light source has allowed practical application of a battery-driven endoscope including a built-in rechargeable battery. A battery-driven endoscope is configured to accommodate a wireless communication unit configured to wirelessly communicate with a processor and wirelessly transmit image data picked up by an image pickup device.

A data quantity transferable over wireless communication (hereinafter also referred to as transferable data quantity) is specified by wireless communication specifications. In an endoscope apparatus including a battery-driven endoscope, image data is transmitted after the image data is compressed so that the data quantity of wirelessly transmitted image data is smaller than or equal to the transferable data quantity.

When a large compression ratio of image data is used to reduce the data quantity of the image data, the image data can be wirelessly transmitted in a stable manner, and electric power consumed by the endoscope can be reduced. However, a large compression ratio of image data degrades image quality of the image data. Therefore, when high-image-quality image data is required, it is desirable to control the compression ratio as needed, for example, to lower the compression ratio.

Japanese Patent No. 6,192,882 describes an endoscope system configured to control the compression ratio of image data based on a state of a scene in which a surgeon performs endoscopic procedures. Japanese Patent No. 6,253,600 describes an endoscope system configured to control the compression ratio of image data based on a pixel value distribution characteristic determined by image pickup characteristics of an image pickup device and spectral characteristics of an object.

SUMMARY OF THE INVENTION

An endoscope apparatus according to an aspect of the present invention includes an image pickup device configured to pick up an image of an object to generate image data, a storage device configured to store the image data, a monitor configured to display a display image corresponding to the image data, and a processor. The processor is configured to carry out a compression processing of compressing the image data by using a compression parameter that is a value that specifies a data quantity after compression to generate compressed data, set the compression parameter based on the compressed data, detect a quantity of information on the object contained in the image data, and carry out a judgement processing of judging whether or not a judgement value corresponding to the quantity of information is smaller than a predetermined threshold. The image pickup of the object and the generation of the image data are continuously performed multiple times. The judgement processing is carried out whenever the image data is generated. The storage device stores the compressed data and a result of the judgement processing. The compression parameter and the display image are determined based on the result of the judgement processing. When the judgement value in the judgement processing is greater than or equal to the predetermined threshold, the display image is an image corresponding to the image data generated when the judgement processing at a current time point is carried out, and when the judgement value in the judgement processing is smaller than the predetermined threshold, the display image is an image corresponding to the image data generated when the judgement processing at the current time point is carried out or an image determined based on a result of the judgement processing at a preceding time point.

An endoscope according to another aspect of the present invention includes an image pickup device configured to pick up an image of an object to generate image data, a storage device configured to store the image data, a wireless communication circuit, and a processor. The processor is configured to carry out a compression processing of compressing the image data by using a compression parameter that is a value that specifies a data quantity after compression to generate compressed data, set the compression parameter based on the compressed data, detect a quantity of information on the object contained in the image data, and carry out a judgement processing of judging whether or not a judgement value corresponding to the quantity of information is smaller than a predetermined threshold. The image pickup of the object and the generation of the image data are continuously performed multiple times. The judgement processing is carried out whenever the image data is generated. The storage device stores the compressed data and a result of the judgement processing. The wireless communication unit transmits the compressed data to the processor to which a display unit configured to display a display image corresponding to the image data is connected. The compression parameter and the display image are determined based on the result of the judgement processing. When the judgement value in the judgement processing is greater than or equal to the predetermined threshold, the display image is an image corresponding to the image data generated when the judgement processing at a current time point is carried out, and when the judgement value in the judgement processing is smaller than the predetermined threshold, the display image is the image corresponding to the image data generated when the judgement processing at the current time point is carried out or an image determined based on a result of the judgement processing at a preceding time point.

An image generation method according to another aspect of the present invention is an image generation method for generating a display image from image data acquired with an image pickup device of an endoscope, the method including carrying out a compression processing of compressing the image data by using a compression parameter that is a value that specifies a data quantity after compression to generate compressed data, storing the image data and the compressed data, setting the compression parameter based on the compressed data, detecting a quantity of information on an object contained in the image data, carrying out a judgement processing of judging whether or not a judgement value corresponding to the quantity of information is smaller than a predetermined threshold, and storing a result of the judgement processing. The image pickup of the object and the generation of the image data are continuously performed multiple times. The judgement processing is carried out whenever the image data is generated. The compression parameter and the display image are determined based on the result of the judgement processing. The image generation method further includes when the judgement value in the judgement processing is greater than or equal to the predetermined threshold, displaying as the display image on a monitor an image corresponding to the image data generated when the judgement processing at a current time point is carried out, and when the judgement value in the judgement processing is smaller than the predetermined threshold, displaying as the display image on the monitor the image corresponding to the image data generated when the judgement processing at the current time point is carried out or an image determined based on a result of the judgement processing at a preceding time point.

DETAILED DESCRIPTION OF THE PREFERRED EMBODIMENTS

Embodiments of the present invention will be described below with reference to the drawings.

Figure 1:
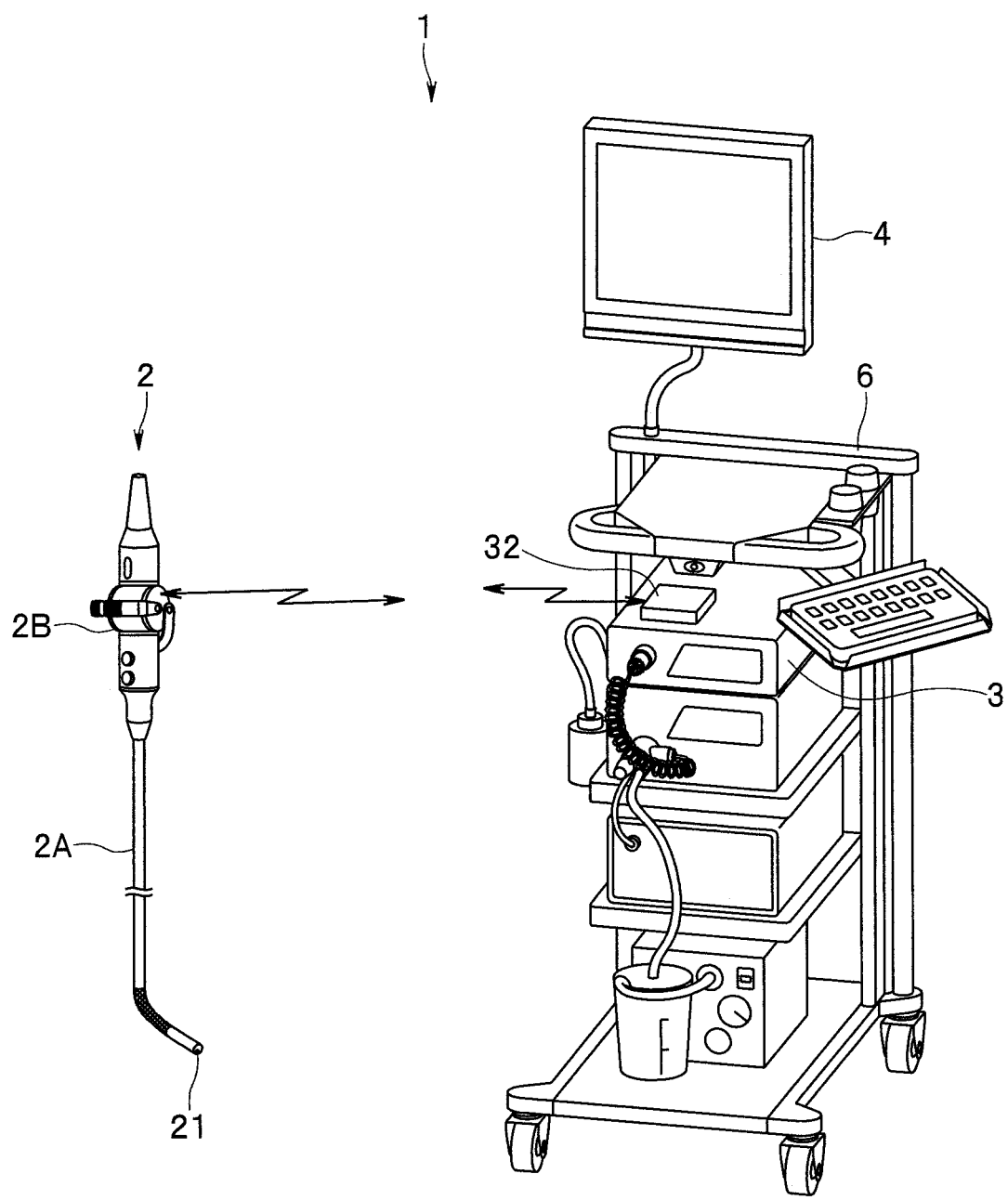
FIG. 1 is a descriptive diagram showing an overall configuration of an endoscope apparatus according to a first embodiment of the present invention.

A general configuration of an endoscope apparatus according to a first embodiment of the present invention will first be described. FIG. 1 is a descriptive diagram showing an overall configuration of an endoscope apparatus 1 according to the present embodiment. The endoscope apparatus 1 according to the present embodiment is a wireless endoscope apparatus including a wireless endoscope 2, which is a battery-driven mobile endoscope. The wireless endoscope 2 will be hereinafter simply referred to as an endoscope 2.

The endoscope apparatus 1 further includes a processor 3, which serves as a video processor physically separate from the endoscope 2, and a monitor 4, which serves as a display unit connected to the processor 3. The processor 3 is wirelessly connected to the endoscope 2 and performs predetermined image processing, which will be described later. The monitor 4 displays a result of the image processing, specifically, for example, an image picked up with the endoscope 2.

The processor 3, the monitor 4, and a variety of types of medical equipment are placed on a cart 6 in a surgery room, as shown in FIG. 1. Examples of the medical equipment placed on the cart 6 include an electrosurgical knife apparatus, a pneumoperitoneum apparatus, a video recorder, and other apparatuses, and a gas cylinder filled with carbon dioxide.

The endoscope 2 includes an elongated insertion section 2A, which is inserted into a body cavity, an operation section 2B, which is provided at a proximal end section of the insertion section 2A, and an image pickup unit 21, which picks up an image of an object and generates image data. The image pickup unit 21 includes an image pickup device, such as a CCD or a CMS device, which is not shown but is provided at a distal end section of the insertion section 2A.

Figure 2:
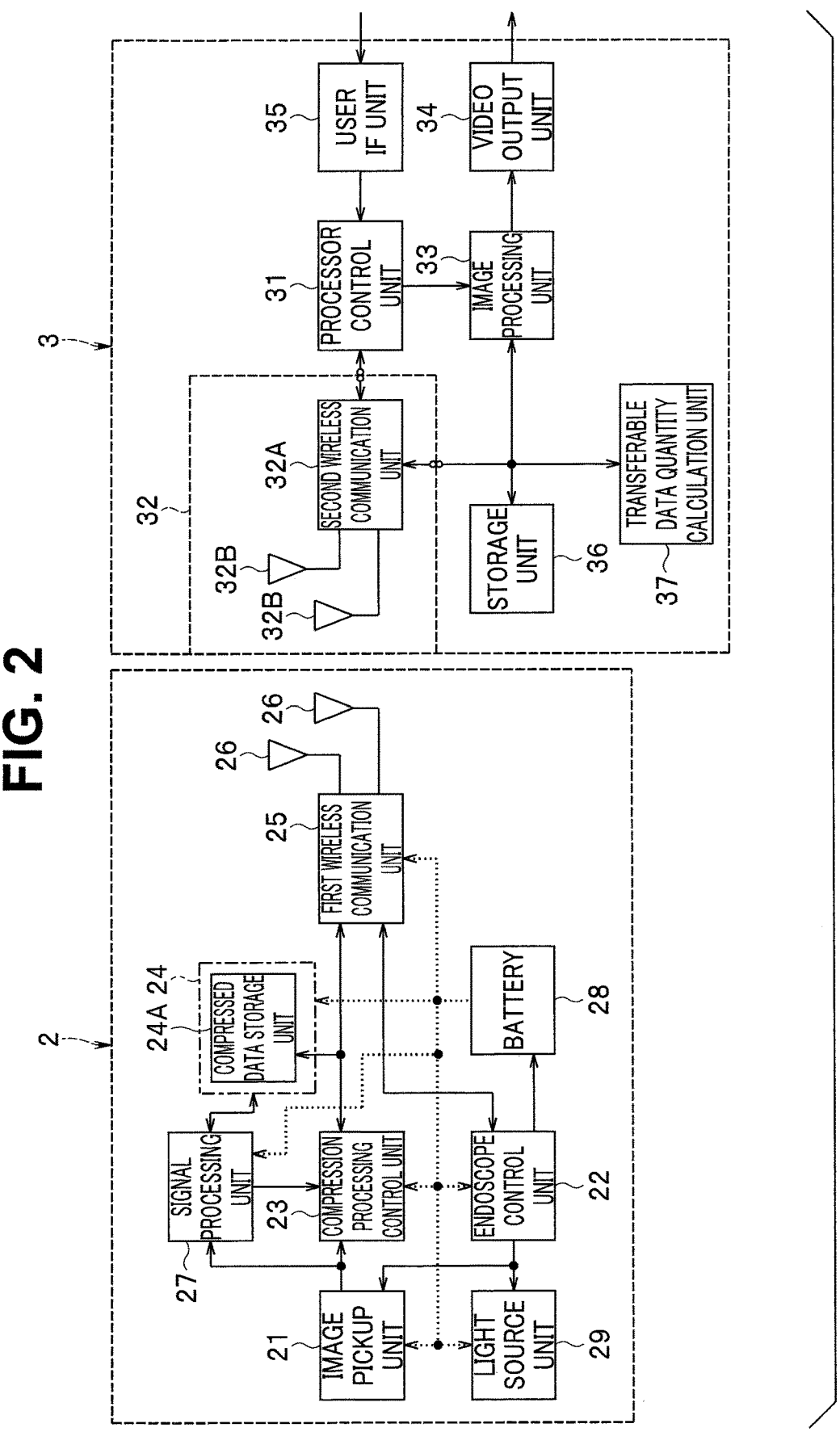
FIG. 2 is a functional block diagram showing configurations of an endoscope and a processor of the endoscope apparatus according to the first embodiment of the present invention.

The configurations of the endoscope 2 and the processor 3 will next be described in detail with reference to FIG. 2. FIG. 2 is a functional block diagram showing the configurations of the endoscope 2 and the processor 3.

(Configuration of Endoscope)

The configuration of the endoscope 2 will first be described. The endoscope 2 includes the image pickup unit 21, an endoscope control unit 22, a compression processing control unit 23, a storage unit 24, a first wireless communication unit 25, antennas 26, a signal processing unit 27, a battery 28, and a light source unit 29, as shown in FIG. 2.

The battery 28 is configured to be attachable to the operation section 2B (see FIG. 1). The battery 28, after attached to the operation section 2B, is configured to serve as a power source unit capable of supplying electric power to the image pickup unit 21, the endoscope control unit 22, the compression processing control unit 23, the storage unit 24, the first wireless communication unit 25, the signal processing unit 27, and the light source unit 29.

The endoscope control unit 22 controls each circuit section in the endoscope 2 and controls the battery 28 to supply each section in the endoscope 2 with the electric power. The endoscope control unit 22 is configured of a processor including hardware, for example, a central processing unit (hereinafter referred to as CPU) or a digital signal processor (hereinafter referred to as DSP).

The light source unit 29 is configured of a light emitting device, such as a light emitting diode, which is not shown but provided at the operation section 2B (see FIG. 1), and produces illumination light with which an interior of a body cavity is illuminated. The illumination light is guided through a light guide that is not shown to a distal end of the insertion section 2A (see FIG. 1) and radiated to an object via a lens that is not shown but is provided at the distal end of the insertion section 2A. The object is, for example, a site of a subject, for example, a diseased site.

The illumination light described above returning from the object is brought into focus at an image pickup surface of the image pickup device of the image pickup unit 21. The image pickup unit 21 generates image data based on an optical image of the object produced by photoelectric conversion and outputs the image data to the compression processing control unit 23 and an information quantity detection unit that will be described later.

The compression processing control unit 23 carries out a compression processing for generating compressed data by carrying out a predetermined compression processing on the image data generated by the image pickup unit 21. The storage unit 24 includes a compressed data storage unit 24A having a predetermined size storage capacity for storing compressed data. In the present embodiment, the storage capacity is fixed. The compression processing control unit 23 is configured of a processor including hardware, for example, a CPU or a DSP. The storage unit 24 is configured of at least part of a rewritable storage device, such as a RANI, provided in the endoscope 2. The content of the compression processing will be described later.

The first wireless communication unit 25 includes a wireless transmission circuit not shown but configured to generate a signal to be wirelessly transmitted and a wireless reception circuit not shown but configured to demodulate a wirelessly received signal, and the first wireless communication unit 25 wirelessly transmits and receives predetermined signals to and from the processor 3 via the antennas 26. The predetermined signals described above each contain the compressed data stored in the compressed data storage unit 24A and transferable data quantity, which will be described later. The first wireless communication unit 25 may be configured to be capable of wireless communication using a plurality of bands, for example, a 60-GHz band and a 5-GHz band. The 60-GHz band is used, for example, to transmit and receive compressed data. The 5-GHz band is used, for example, to transmit and receive information excluding compressed data.

(Configuration of Signal Processing Unit)

Figure 3:
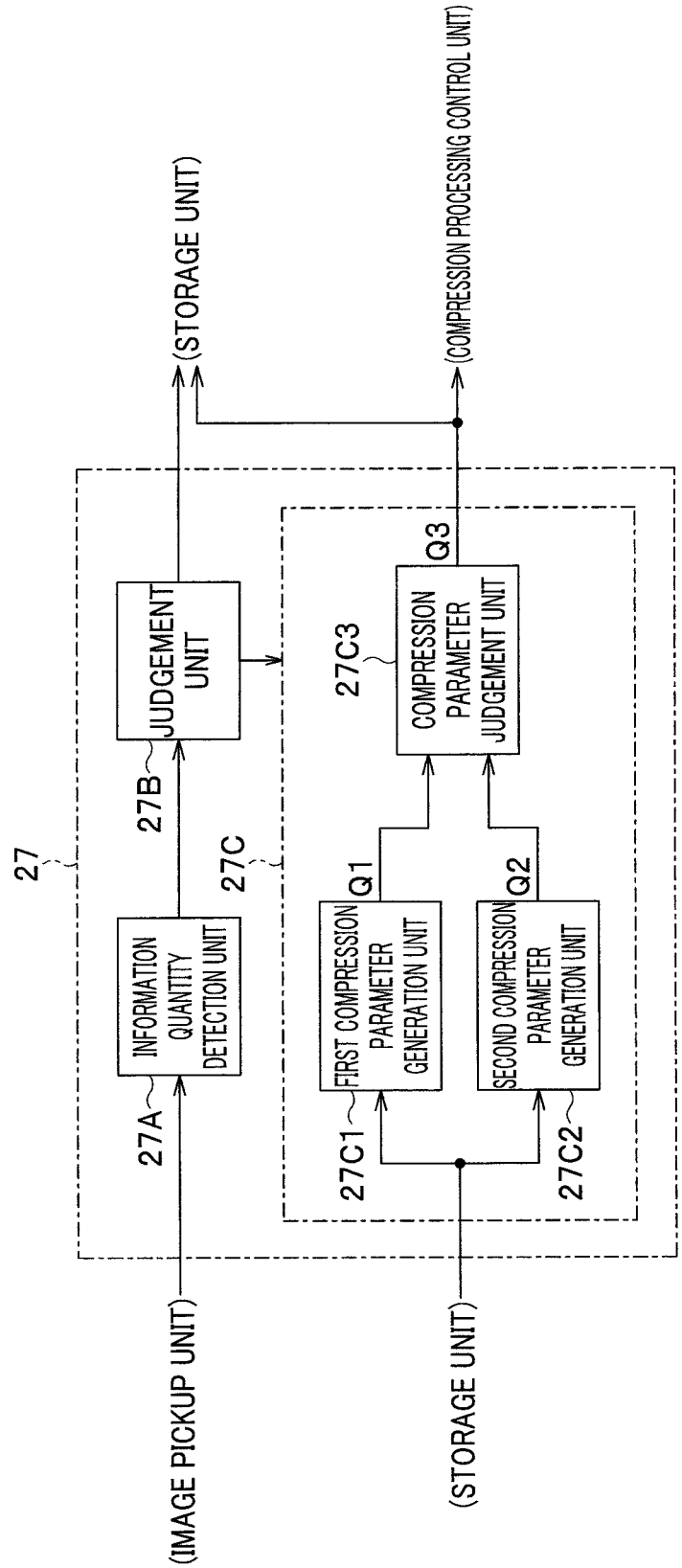
FIG. 3 is a functional block diagram showing a configuration of a signal processing unit in the first embodiment of the present invention.

The configuration of the signal processing unit 27 will be described with reference to FIG. 3. FIG. 3 is a functional block diagram showing the configuration of the signal processing unit 27. The signal processing unit 27 is configured of a processor including hardware, for example, a CPU or a DSP. In the present embodiment, the signal processing unit 27 includes an information quantity detection unit 27A, a judgement unit 27B, and a parameter setting unit 27C. Since the signal processing unit 27 is part of the endoscope 2, it can be said that the endoscope 2 is provided with the information quantity detection unit 27A, the judgement unit 27B, and the parameter setting unit 27C.

The image data picked up by the image pickup unit 21 is inputted to the information quantity detection unit 27A. The information quantity detection unit 27A detects a quantity of information on the object contained in the image data and outputs the object information quantity to the judgement unit 27B. The judgement unit 27B carries out a predetermined judgement processing based on the object information quantity and outputs a judgement result to the storage unit 24 and the parameter setting unit 27C. The storage unit 24 stores the judgement result. A method for detecting the information quantity and the judgement processing will be described later in detail.

The parameter setting unit 27C sets compression parameters used in the compression processing control unit 23 based on the judgement result from the judgement unit 27B and the compressed data stored in the compressed data storage unit 24A (see FIG. 2). The parameter setting unit 27C includes a first compression parameter generation unit 27C1, a second compression parameter generation unit 27C2, and a compression parameter judgement unit 27C3.

The first compression parameter generation unit 27C1 and the second compression parameter generation unit 27C2 are each configured to be capable of acquiring a data quantity of the compressed data stored in the compressed data storage unit 24A. The first compression parameter generation unit 27C1 generates a first provisional compression parameter Q1 and outputs the first provisional compression parameter Q1 to the compression parameter judgement unit 27C3. The second compression parameter generation unit 27C2 generates a second provisional compression parameter Q2 and outputs the second provisional compression parameter Q2 to the compression parameter judgement unit 27C3.

The compression parameter judgement unit 27C3 compares the first provisional compression parameter Q1 with the second provisional compression parameter Q2, selects one of the compression parameters as a compression parameter used in the compression processing, and sets the selected compression parameter as a setting parameter Q3. The compression parameter judgement unit 27C3 outputs the setting parameter Q3 to the compression processing control unit 23 and the selected compression parameter to the storage unit 24. The storage unit 24 stores the selected compression parameter. A method for setting the setting parameter Q3 will be described later.

(Configuration of Processor)

The configuration of the processor 3 will next be described. The processor 3 includes a processor control unit 31, a wireless receiver 32, an image processing unit 33, a video output unit 34, a user interface unit (hereinafter referred to as user IF unit) 35, a storage unit 36, and a transferable data quantity calculation unit 37, as shown in FIG. 2.

The wireless receiver 32 may be built in the processor 3 or may be configured to be a component separate from a main body of the processor 3. In the latter case, the wireless receiver 32 is configured to be connected to the main body of the processor 3 via a connector that is not shown. FIG. 1 shows an example of the configuration in which the wireless receiver 32 is a component separate from the main body of the processor 3.

The wireless receiver 32 includes a second wireless communication unit 32A and antennas 32B. Since the wireless receiver 32 is part of the processor 3, it can be said that the processor 3 is provided with the second wireless communication unit 32A.

The second wireless communication unit 32A includes a wireless transmission circuit not shown but configured to generate a signal to be wirelessly transmitted and a wireless reception circuit not shown but configured to demodulate a wirelessly received signal, and the second wireless communication unit 32A wirelessly transmits and receives predetermined signals to and from the endoscope 2 via the antennas 32B. The predetermined signals described above contain compressed data transmitted by the first wireless communication unit 25 and the transferable data quantity, which will be described later. The second wireless communication unit 32A may be configured to be capable of wireless communication using a plurality of bands, for example, the 60-GHz band and the 5-GHz band, as the first wireless communication unit 25.

The storage unit 36 has a predetermined size storage capacity and stores the compressed data received by the second wireless communication unit 32A and decompressed image data, which will be described later. The storage unit 36 is configured of at least part of a rewritable storage device, such as a RAM, provided in the processor 3.

The image processing unit 33 reads the compressed data from the storage unit 36 and performs predetermined image processing on the compressed data. Specifically, the image processing unit 33 decompresses the compressed data to generate image data. Uncompressed image data generated by the image processing unit 33 is hereinafter referred to as decompressed image data.

The image processing unit 33 outputs the decompressed image data to the monitor 4 via the video output unit 34. The video output unit 34 converts a format of the decompressed image data into a format displayable on the monitor 4. The monitor 4 displays a display image corresponding to the decompressed image data.

The image processing unit 33 may output the decompressed image data to the storage unit 36. In this case, the storage unit 36 stores the decompressed image data.

The user IF unit 35 is an interface configured to accept a user's operation. Specifically, the user IF unit 35 is configured, for example, of a front panel and a variety of buttons of a control system and outputs an operation signal based on the user's operation to the processor control unit 31. Examples of the user's operation include specification of an observation mode of the endoscope 2, settings on image display, and setting of initial values of the compression parameters, which will be described later. A user IF unit may be provided in the endoscope 2, and the observation mode of the endoscope 2 may be specified via at least one of the user IF unit 35 of the processor 3 or the user IF unit of the endoscope 2.

The processor control unit 31 controls each circuit section in the processor 3 and a power source unit that is not shown to cause the power source unit to supply each portion in the processor 3 with electric power. The processor control unit 31 can issue a variety of instructions to the endoscope control unit 22 provided in the endoscope 2 via wireless communication between the endoscope 2 and the processor 3 based on an operation signal inputted via the user IF unit 35.

The transferable data quantity calculation unit 37 successively calculates the transferable data quantity, which is a quantity of data transferable along a transmission path along which image data is transmitted, and outputs the calculated transferable data quantity to the storage unit 24 of the endoscope 2 via the wireless communication between the endoscope 2 and the processor 3. The storage unit 24 stores the transferable data quantity.

The transferable data quantity is specified, for example, by a data quantity transferable in a time period for which image data corresponding to one frame is transmitted. In the present embodiment, the transmission path includes a wireless transmission path formed between the antennas 26 and the antennas 32B.

The transferable data quantity in wireless communication is specified by specifications of the wireless communication and changes depending on an environment of the wireless communication. In the present embodiment, the transferable data quantity calculation unit 37 calculates the transferable data quantity based on the environment of the wireless communication. Specifically, for example, data for calculation may be transmitted and received between the endoscope 2 and the processor 3 with the quantity of the data changed, and the transferable data quantity may be calculated from the data quantity of the data for calculation having been successfully transmitted and received. The data for calculation may be the image data generated by the image pickup unit 21. In this case, the image processing unit 33 and the transferable data quantity calculation unit 37 are configured so that the data quantity of the image data decompressed by the image processing unit 33 is outputted to the transferable data quantity calculation unit 37.

The processor control unit 31, the image processing unit 33, and the transferable data quantity calculation unit 37 are each configured of a processor including hardware, for example, a CPU or a DSP.

(Image Data Processing in Endoscope)

Figure 4:
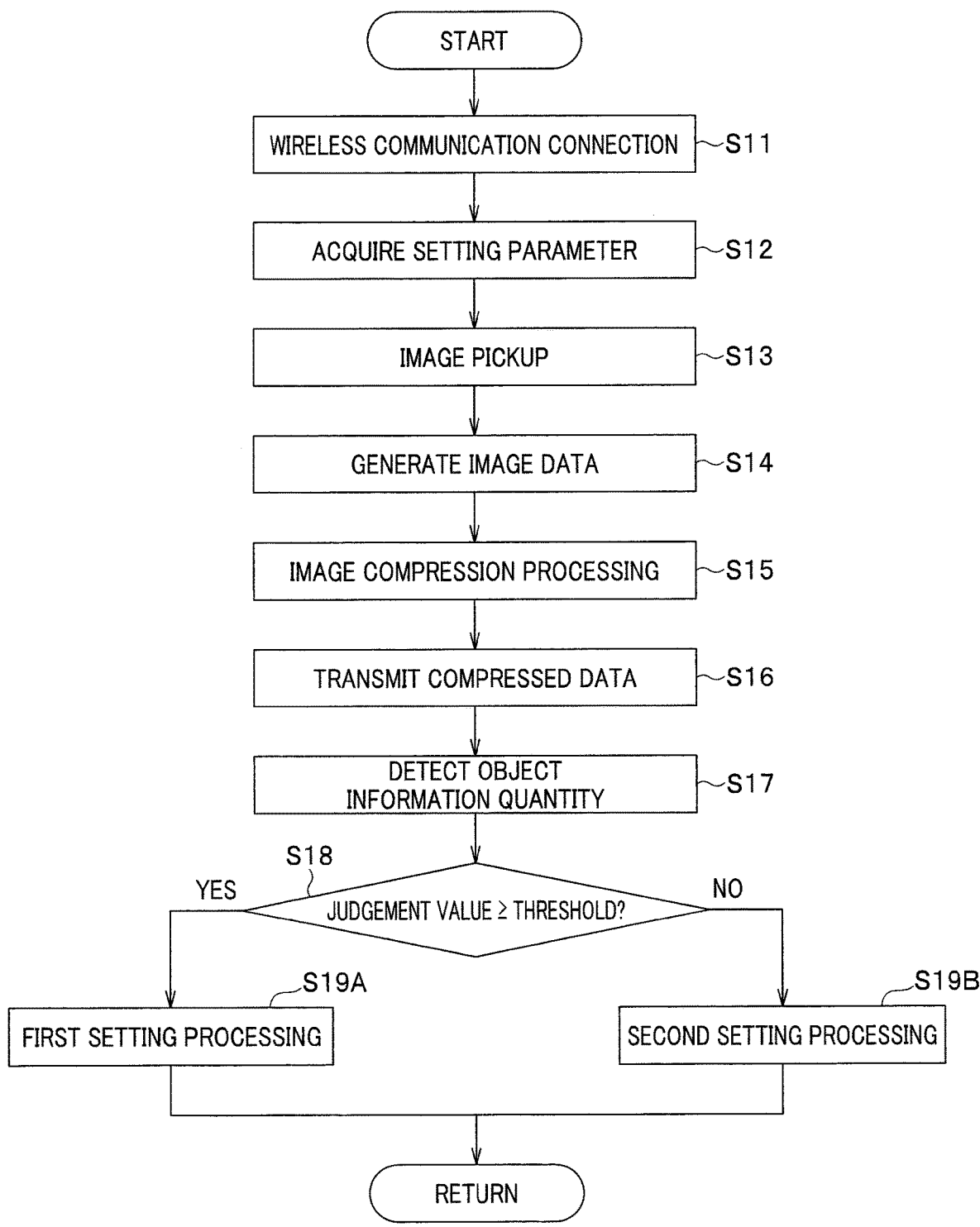
FIG. 4 is a flowchart showing an image data processing procedure in the endoscope shown in FIG. 2.

An image data processing procedure in the endoscope 2 will next be described with reference to FIGS. 2 to 4. FIG. 4 is a flowchart showing the image data processing procedure in the endoscope 2. The image data processing in the endoscope 2 includes a compression processing in the compression processing control unit 23, a processing of detecting the object information quantity in the information quantity detection unit 27A, a judgement processing in the judgement unit 27B, and a parameter setting processing in the parameter setting unit 27C.

The image data processing in the endoscope 2 is performed by the endoscope control unit 22, the compression processing control unit 23, and the signal processing unit 27. The image data processing in the endoscope 2 is initiated when an operation signal based on the user's operation instructing initiation of an image pickup processing is inputted to the endoscope control unit 22, and a series of processes shown in FIG. 4 are repeatedly carried out until an operation signal based on the user's operation instructing end of the image pickup processing is inputted to the endoscope control unit 22. In the present embodiment, the series of processes described above are carried out once whenever one set of image data is generated by the image pickup unit 21. The operation signals are, for example, outputted from the user IF unit not shown but provided in the endoscope 2 or the user IF unit 35 provided in the processor 3.

In the image data processing in the endoscope 2, the endoscope control unit 22 first establishes wireless communication connection between the endoscope 2 and the processor 3 (step S11). In the image data processing performed N-th time (N is integer greater than or equal to 2), whether the wireless communication connection is maintained in place of the processing of establishing the wireless communication connection. When the wireless communication connection is not maintained, the processing of establishing the wireless communication connection may be carried out. When the wireless communication connection is maintained, the processing of establishing the wireless communication connection may be omitted.

The compression processing control unit 23 then acquires the setting parameter Q3 (step S12) set in steps S19A and S19B, which will be carried out later. The setting parameter Q3 may be acquired directly from the parameter setting unit 27C or may be acquired from the storage unit 24. In the image data processing performed first, the compression processing control unit 23 acquires in place of the setting parameter Q3 an initial value Qi of the compression parameter. The initial value Qi may be a set value inputted to the user IF unit 35 or a set value stored in the storage unit 24.

The endoscope control unit 22 then controls the image pickup unit 21 to pick up an image of the object to generate image data by using as a power source the electric power supplied from the battery 28 (steps S13 and S14). The image data is outputted to the compression processing control unit 23 and the information quantity detection unit 27A. The image data may, for example, be raw data.

The compression processing control unit 23 then carries out an image compression processing of compressing the image data to generate compressed data (step S15). The compression processing control unit 23 outputs the generated compressed data to the compressed data storage unit 24A. The compressed data storage unit 24A stores the compressed data. The endoscope control unit 22 then controls the first wireless communication unit 25 to transmit the compressed data stored in the compressed data storage unit 24A to the processor 3 (step S16). The processes in steps S15 and S16 will be described later in detail.

The information quantity detection unit 27A of the signal processing unit 27 then carries out a processing of detecting the quantity of the information on the object contained in the image data (step S17). The information quantity detection unit 27A may output the detected information quantity to the storage unit 24. The storage unit 24 stores the detected information quantity.

The object information quantity will now be described in detail. The object information quantity is a quantity of information on a normally picked-up image of the object contained in the image data, and the larger a quantity of information on an image of objects excluding the normally picked-up image of the object, the smaller the object information quantity. The object information quantity may be expressed, for example, by a value greater than or equal to 0 but smaller than or equal to 1, with 0 corresponding to a case where no diseased site (object) of a subject has been picked up and 1 corresponding to a case where an entire diseased site of the subject has been normally picked up. Examples of the information on an image of objects excluding the normally picked-up image of the object include information on an image of an object not having been successfully picked up due, for example, to halation and information on an image of an object having been picked up but blurred due, for example, to liquid or smoke or due to defocusing.

In the present embodiment, the object information quantity is specified based on at least one of color information contained in image data, resolution of the image data, or the data quantity of compressed data. The color information contained in image data is, for example, information on chroma or contrast of an image. The information on an image of an object not having been picked up due, for example, to halation is image information with the chroma or the contrast lost. The color information, such as the chroma or the contrast, therefore allows estimation of the object information quantity and the quantity of the information on the objects excluding the normally picked-up object. To specify the object information quantity based on the color information contained in the image data, the information quantity detection unit 27A detects a value relating to numerical color information as the object information quantity.

The resolution of image data is an index representing minuteness of the image data. The resolution of image data can be expressed, for example, by an edge quantity. The edge quantity is a quantity of a portion where brightness of an image discontinuously changes. In information on an image of an object having been picked up but blurred, the edge quantity decreases, and the resolution also decreases. The resolution therefore allows estimation of the object information quantity and the quantity of the information on the objects excluding the normally picked-up object. To specify the object information quantity based on the resolution of the image data, the information quantity detection unit 27A detects a value relating to the resolution as the object information quantity.

An image of an object not having been successfully picked up and an image of an object having been picked up but blurred are each a monotonous image as compared with an image having been normally picked up. When image data having a small object information quantity is compressed to generate compressed data, the data quantity of compressed data is smaller than the data quantity of compressed data generated by compressing normally picked-up image data. The data quantity of compressed data therefore allows estimation of the object information quantity and the quantity of the information on the objects excluding the normally picked-up object. To specify the object information quantity based on the data quantity of the compressed data, the information quantity detection unit 27A detects a value relating to the data quantity of the compressed data as the object information quantity.

The compression parameters relate to the data quantity of compressed data. When the compression parameters are generated based on image data on an object not having been normally picked up, that is, when the compression parameters are generated based on compressed data having a small data quantity, the compression parameters each have a small value. In other words, a case where the compression parameters each have an extremely small value or a case where current compression parameters are extremely smaller than preceding compression parameters can be estimated as a case where the quantity of the information on the object contained in the image data is small, that is, the object has not been normally picked up. Therefore, to specify the object information quantity based on the data quantity of the compressed data, the information quantity detection unit 27A may generate the compression parameters by using the same method as a method for a compression parameter generation processing that will be described later and detect a value relating to the compression parameters as the object information quantity.

When the data quantity of preceding compressed data is greater than the transferable data quantity, the values of the current compression parameters are smaller than the values of the preceding compression parameters even when the object has been normally picked up. For example, when the data quantity of preceding compressed data is extremely large, differences between the preceding compression parameters and the current compression parameters also extremely increase. Therefore, when the object information quantity is detected by comparing the preceding compression parameters with the current compression parameters, and when the data quantity of the preceding compressed data is extremely large, the object information quantity is not detected as an exception by comparing the preceding compression parameters with the current compression parameters.

Information on colors contained in image data and the resolution of the image data can be acquired by causing the information quantity detection unit 27A to analyze the image data. The data quantity of compressed data can be acquired by causing the information quantity detection unit 27A to read the data quantity of compressed data stored in the compressed data storage unit 24A. To specify the object information quantity based on the data quantity of the compressed data, the information quantity detection unit 27A and the compressed data storage unit 24A are configured to be capable of acquiring the data quantity of the compressed data stored in the compressed data storage unit 24A.

In image data processing in the endoscope 2, the judgement unit 27B of the signal processing unit 27 carries out a judgement processing of judging whether or not a judgement value relating to the object information quantity detected by the information quantity detection unit 27A is smaller than a predetermined threshold (step S18). The judgement value may be the information quantity or a difference between the information quantity detected when a current judgement processing (judgement processing carried out N-th time) is carried out and the information quantity detected when a preceding judgement processing (judgement processing carried out (N−1)-th time) is carried out. In a latter case, the judgement unit 27B reads the information quantity generated when the preceding judgement processing is carried out from the storage unit 24 to generate the judgement value. Further, in the latter case, in the judgement processing carried out first, a predetermined value stored in the storage unit 24 is used in place of the information quantity generated when the preceding judgement processing is carried out. The judgement unit 27B outputs a judgement result to the storage unit 24 and the parameter setting unit 27C.

In the judgement processing, when the judgement value is greater than or equal to the predetermined threshold (YES), it can be judged that the object information quantity is sufficient, that is, the object has been normally picked up. On the other hand, in the judgement processing, when the judgement value is smaller than the predetermined threshold (NO), it can be judged that the object information quantity is insufficient, that is, the object has not been normally picked up.

The parameter setting unit 27C of the signal processing unit 27 then carries out a parameter setting processing based on the judgement result from the judgement unit 27B. When the judgement value is greater than or equal to the predetermined threshold (YES), the parameter setting unit 27C carries out a first setting processing (step S19A), and when the judgement value is smaller than the predetermined threshold (NO), the parameter setting unit 27C carries out a second setting processing (step S19B).

In the first setting processing, the parameter setting unit 27C generates a compression parameter based on compressed data corresponding to image data generated when the current judgement processing (judgement processing carried out N-th time) and sets the generated compression parameter as the setting parameter Q3. In the present embodiment, the compression parameter selected by the compression parameter judgement unit 27C3 corresponds to the compression parameter generated as described above. The parameter setting unit 27C outputs the generated compression parameter to the storage unit 24. Whenever the compression parameter is generated, the storage unit 24 stores the generated compression parameter. A method for generating the compression parameter will be described later.

In the second setting processing, the parameter setting unit 27C reads the compression parameter from the storage unit 24 based on a result of the preceding judgement processing (judgement processing carried out (N−1)-th time) and sets the read compression parameter as the setting parameter Q3. When the judgement value is smaller than the predetermined threshold in the first judgement processing, the parameter setting unit 27C reads a predetermined set value stored in the storage unit 24 in the second setting processing and sets the set value as the setting parameter Q3. The set value may be equal to or different from the initial value Qi. The parameter setting unit 27C does not carry out the processing of generating a compression parameter when the judgement value is smaller than the predetermined threshold.

When the judgement value is greater than or equal to the predetermined threshold in the preceding judgement processing (judgement processing carried out (N−1)-th time), it can be judged that the quantity of the information on the object contained in image data generated (N−1)-th time is sufficient, that is, the object has been normally picked up (N−1)-th time. In this case, the parameter setting unit 27C sets as the setting parameter Q3 a compression parameter generated based on compressed data corresponding to image data generated when the preceding judgement processing is carried out. When the judgement value is smaller than the predetermined threshold in the preceding judgement processing, it can be judged that the quantity of the information on the object contained in the image data generated (N−1)-th time is insufficient, that is, the object has not been normally picked up (N−1)-th time. In this case, the parameter setting unit 27C sets as the setting parameter Q3 a compression parameter corresponding to image data generated prior to the preceding judgement processing that is a judgement processing providing a judgement value greater than or equal to the predetermined threshold is carried out.

In the image data processing in the endoscope 2, when an operation signal based on the user's operation of instructing end of the image pickup processing is not inputted to the endoscope control unit 22 after step S19A or step S19B, the endoscope control unit 22 returns to step S11, whereas when the operation signal described above is inputted to the endoscope control unit 22, the endoscope control unit 22 terminates the image data processing in the endoscope 2.

A description has been made of an example in which the compression processing in the compression processing control unit 23, the processing of detecting the object information quantity in the information quantity detection unit 27A, the judgement processing in the judgement unit 27B, and the parameter setting processing in the parameter setting unit 27C are carried out as the series of processes. However, the procedure of the image data processing in the endoscope 2 is not limited to the example shown in FIG. 4. For example, a series of processes from steps S11 to step S16 and a series of processes from step S17 to step S19A or step 19B may be carried out separately from each other. In this case, the series of processes from steps S17 to step S19A or step 19B are carried out once whenever the image pickup unit 21 generates image data.

The order in accordance with which the steps in the image data processing procedure in the endoscope 2 are carried out is also not limited to the example shown in FIG. 4. For example, the processing of establishing the wireless communication connection (step S11) and the processing of acquiring the setting parameter Q3 (step S12) may be carried out after the processing of picking up an object to generate image data (step S13, S14). In this case, the image compression processing (step S15) is carried out after the processing of acquiring the setting parameter Q3.

(Compression Process and Transmission Process)

A series of processes in steps S15 and S16 will be described now in detail. In the present embodiment, the compression processing control unit 23 compresses image data for each of a plurality of unit areas of the image data and generates a plurality of compressed portions as the compressed data from single image data. The single image data corresponds to a single-frame image.

When the series of processes shown in FIG. 4 are carried out N times, the compression processing is also carried out N times. In the compression processing carried out N-th time, the compression processing control unit 23 first updates the compression parameter Q to the setting parameter Q3 acquired in step S12. In other words, the compression processing control unit 23 sets the setting parameter Q3 as a new compression parameter Q. Note that, in the compression processing carried out first, the compression processing control unit 23 sets the initial value Qi as the compression parameter Q.

When the judgement value is smaller than the predetermined threshold in the judgement processing carried out N-th time (step S18), the compression processing control unit 23 in step S12 carried out (N+1)-th time acquires the setting parameter Q3 having a value equal to the value of the setting parameter Q3 acquired in step S12 carried out (N+1)-th time or before. In this case, the compression processing control unit 23 may or may not carry out the processing of updating the compression parameter Q. In either case, the compression parameter Q is not substantially updated. In other words, the compression processing control unit 23 updates the compression parameter Q to the setting parameter Q3 when the judgement value is greater than or equal to the predetermined threshold and does not update the compression parameter Q when the judgement value is smaller than the predetermined threshold.

In the series of processes in steps S15 and S16, the compression processing control unit 23 then divides the image data into a plurality of areas. A method for dividing image data into a plurality of areas is, for example, a method for performing raster scanning on the image data. The compression processing control unit 23 then compresses the image data on a unit area basis by using the compression parameter Q to generate a plurality of compressed portions as the compressed data from single image data.

The compression parameter Q is a value that specifies the data quantity after the compression. A compression format can be an arbitrary image compression format. The compression parameter Q relates to a parameter that specifies a compression ratio in the compression format. In the present embodiment, the compression parameter Q is specified so that the compression ratio increases as the value of the compression parameter Q increases, that is, the data quantity after the compression decreases as the value of the compression parameter Q increases.

The data quantity after the compression changes in accordance not only with the value of the compression parameter Q but with a difference in image information contained in a unit area. In other words, even in a case where the value of the compression parameter Q is the same and the unit areas have the same data quantity, but when the image information contained in any of the unit areas differs from the image information contained in the other unit areas, the data quantities in the plurality of compressed portions differ from one another.

In the series of processes in steps S15 and S16, the plurality of compressed portions are each temporarily saved in the compressed data storage unit 24A. Specifically, the compression processing control unit 23 sequentially outputs the plurality of compressed portions to the compressed data storage unit 24A, and the compressed data storage unit 24A sequentially stores the plurality of outputted compressed portions. The endoscope control unit 22 then controls the first wireless communication unit 25 to sequentially read and transmit the plurality of compressed portions stored in the compressed data storage unit 24A.

As described above, the compressed data storage unit 24A is used as a memory configured to temporarily save the compressed data (plurality of compressed portions). The first wireless communication unit 25 reads and transmits one compressed portion for each of a plurality of unit packets. In other words, to transmit a compressed portion, the first wireless communication unit 25 first reads part of the compressed portions from the compressed data storage unit 24A, generates a wireless signal, and transmits the wireless signal. The first wireless communication unit 25 then sequentially carries out the same processing on the plurality of other compressed portions.

(Image Data Processing in Processor)

Figure 5:
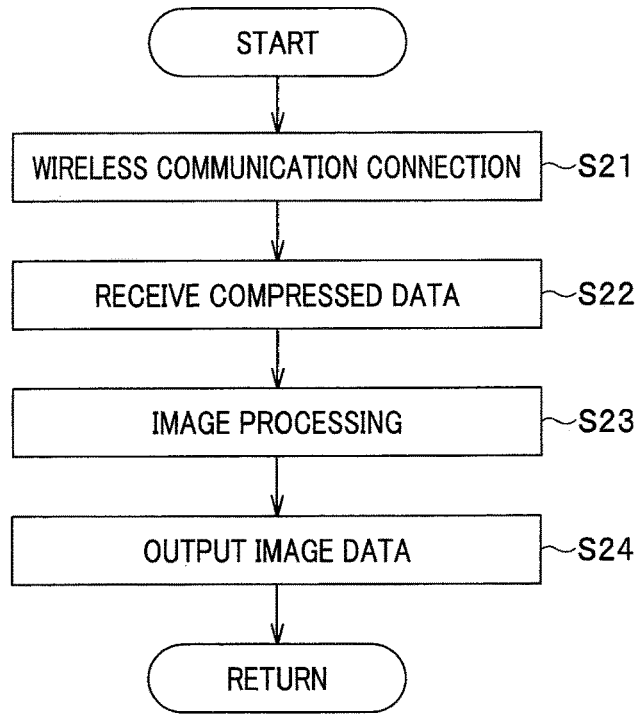
FIG. 5 is a flowchart showing an image data processing procedure in the processor shown in FIG. 2.

An image data processing procedure in the processor 3 will next be described with reference to FIGS. 2 and 5. FIG. 5 is a flowchart showing the image data processing procedure in the processor 3.

In the image data processing in the processor 3 is performed by the processor control unit 31 and the image processing unit 33. The image data processing in the processor 3 is initiated when an operation signal based on the user's operation instructing initiation of the image pickup processing is inputted to the processor control unit 31, and a series of processes shown in FIG. 5 are repeatedly carried out until an operation signal based on the user's operation instructing end of the image pickup processing is inputted to the processor control unit 31, as in the image data processing in the endoscope 2. In the present embodiment, the series of processes described above are carried out once whenever one set of image data is generated by the image pickup unit 21.

In the image data processing in the processor 3, the processor control unit 31 first establishes the wireless communication connection between the endoscope 2 and the processor 3 (step S21). In the image data processing performed N-th time (N is integer greater than or equal to 2), whether the wireless communication connection is maintained is checked in place of the processing of establishing the wireless communication connection, and when the wireless communication connection is not maintained, the processing of establishing the wireless communication connection may be carried out. When the wireless communication connection is maintained, the processing of establishing the wireless communication connection may be omitted.

The processor control unit 31 then controls the second wireless communication unit 32A to receive the compressed data, that is, the plurality of compressed portions transmitted by the first wireless communication unit 25 (step S22). The received plurality of compressed portions (compressed data) are stored in the storage unit 36.

The image processing unit 33 then reads the compressed data from the storage unit 36 and performs predetermined image processing on the compressed data (step S23). Specifically, the image processing unit 33 decompresses each of the plurality of compressed portions and link the decompressed data to each other to generate non-compressed image data (decompressed image data).

The image processing unit 33 then outputs the decompressed image data to the monitor 4 (step S24). The image processing unit 33 may output the decompressed image data to the storage unit 36. In this case, the storage unit 36 stores the decompressed image data.

When the operation signal based on the user's operation instructing end of the image pickup processing is not inputted to the processor control unit 31, the processor control unit 31 returns to step S21, whereas when the operation signal described above is inputted to the processor control unit 31, the processor control unit 31 terminates the image data processing in the processor 3.

(Processing of Generating Compression Parameters)

A processing of generating the compression parameters will next be described. In the present embodiment, the processing of generating the compression parameters includes a first provisional compression parameter generation processing, a second provisional compression parameter generation processing, and a compression parameter selection processing. The first provisional compression parameter generation processing and the second provisional compression parameter generation processing are carried out in an arbitrary order. The compression parameter selection processing is carried out after both the first provisional compression parameter generation processing and the second provisional compression parameter generation processing are carried out.

(First Provisional Compression Parameter Generation Processing)

Figure 6:
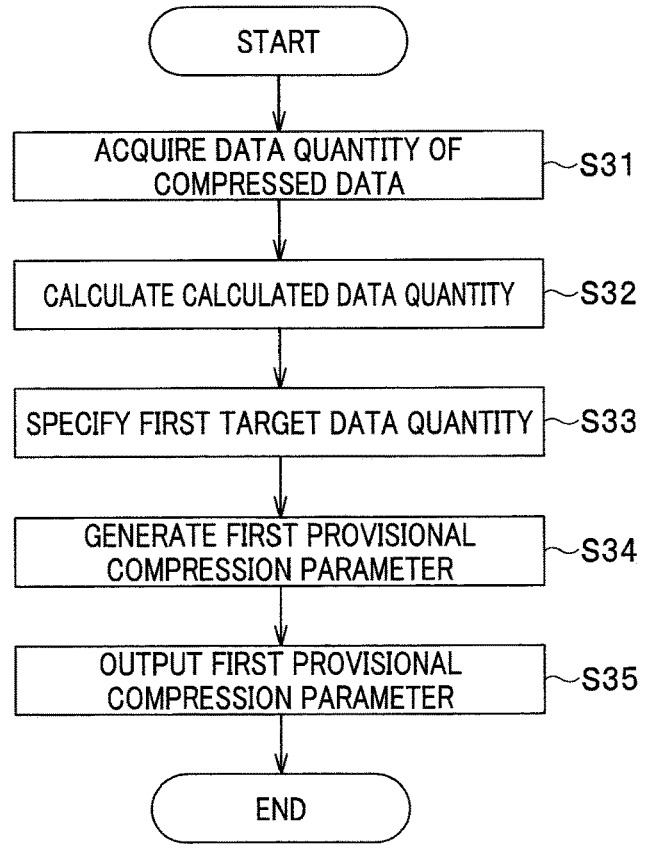
FIG. 6 is a flowchart showing a procedure of a first provisional compression parameter generation processing in the first embodiment of the present invention.

The first provisional compression parameter generation processing will first be described with reference to FIGS. 2, 3, and 6. FIG. 6 is a flowchart showing a procedure of the first provisional compression parameter generation processing. The first provisional compression parameter generation processing is carried out by the first compression parameter generation unit 27C1. In the first provisional compression parameter generation processing, the first compression parameter generation unit 27C1 first acquires the data quantity of the compressed data stored in the compressed data storage unit 24A (step S31). The data quantity of the compressed data is the sum of the data quantities of the plurality of compressed portions.

The first compression parameter generation unit 27C1 then calculates a calculated data quantity V1, which relates to the data quantity of compressed data (step S32). It is assumed in the present embodiment that the data quantity of compressed data is the calculated data quantity V1.

The first compression parameter generation unit 27C1 then acquires the transferable data quantity from the storage unit 24 and specifies a first target data quantity T1 based on the transferable data quantity (step S33). The first target data quantity T1 is specified to be smaller than the transferable data quantity, for example, by subtracting a predetermined value from the transferable data quantity or multiplying the transferable data quantity by a predetermined coefficient smaller than 1. The first target data quantity T1 may be specified based on, in addition to the transferable data quantity, at least one of a distribution characteristic of pixel values in each color signal representing colors in image data, a scene captured by the endoscope, or a wireless environment. The distribution characteristic of the pixel values is determined by image pickup characteristics of the image pickup device and spectroscopic characteristics of the object.

The first compression parameter generation unit 27C1 then generates the first provisional compression parameter Q1 by performing first computation of calculating a compression parameter for compressing the image data in such a way that the calculated data quantity V1 is smaller than or equal to the first target data quantity T1 (step S34). The first computation is expressed, for example, by Equation (1) below.

$$Q1(n)=Q3(n-1)+A1*(V1-T1)/T1 \qquad (1)$$

In Equation (1), $Q1(n)$ represents the first provisional compression parameter Q1 calculated n-th time when the first setting processing (step S19A) shown in FIG. 4 is carried out n times (n is integer greater than or equal to 1). $Q3(n-1)$ represents the setting parameter Q3 set (n−1)-th time. $Q3(n-1)$ corresponds to the first provisional compression parameter Q1 calculated (n−1)-th time or the second provisional compression parameter Q2 calculated (n−1)-th time. The first compression parameter generation unit 27C1 reads $Q3(n-1)$ from the storage unit 24 and calculates $Q1(n)$. A1 is a positive integer.

Note that a first provisional compression parameter $Q1(1)$ calculated first is calculated by using a predetermined constant in place of $Q3(n-1)$ in Equation (1). The predetermined constant may be the initial value Qi.

The reason why using the first provisional compression parameter Q1 calculated by using Equation (1) allows the compression processing to be carried out so that the calculated data quantity V1 is smaller than or equal to the first target data quantity T1 is as follows: In other words, the calculated data quantity V1 corresponds to the calculated data quantity by using $Q3(n-1)$ as the compression parameter. As will be seen from Equation (1), when the calculated data quantity V1 is greater than the first target data quantity T1, $Q1(n)$ is greater than $Q3(n-1)$. As a result, the calculated data quantity calculated by using $Q1(n)$ as the compression parameter decreases. Appropriate selection of a value of A1 allows the calculated data quantity calculated by using $Q1(n)$ as the compression parameter to be smaller than or equal to the first target data quantity T1. In the present embodiment, the first provisional compression parameter Q1, which is a compression parameter for compressing the image data in such a way that the calculated data quantity V1 is smaller than or equal to the first target data quantity T1, is generated as described above.

Note that as will be seen from Equation (1), when the calculated data quantity V1 is smaller than the first target data quantity T1, $Q1(n)$ is smaller than $Q3(n-1)$, resulting in an increase in the calculated data quantity calculated by using $Q1(n)$ as the compression parameter. As the value of A1, a value that does not cause the calculated data quantity calculated by using $Q1(n)$ as the compression parameter is not too large is selected. As will be seen from Equation (1), when the calculated data quantity V1 is equal to the first target data quantity T1, $Q1(n)$ is equal to $Q3(n-1)$.

In the first provisional compression parameter generation processing, the first compression parameter generation unit 27C1 then outputs the first provisional compression parameter Q1 to the compression parameter judgement unit 27C3 (step S35). The first provisional compression parameter generation processing thus ends.

A method for calculating the first provisional compression parameter Q1 is not limited to the example shown in Equation (1). For example, in place of A1 in Endoscope (1), the first provisional compression parameter Q1 may be calculated by using a parameter that changes depending to at least one of the pixel value distribution characteristic, the scene captured by the endoscope, or the wireless environment. As the calculated data quantity V1, an average of the data quantities in the plurality of compressed portions may be used in place of the data quantity of the compressed data.

(Second Provisional Compression Parameter Generation Processing)

Figure 7:
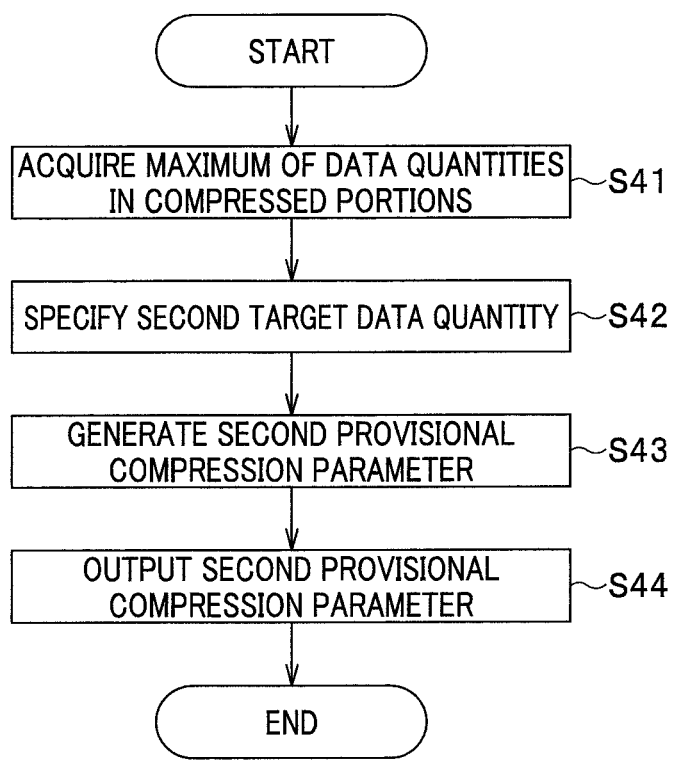
FIG. 7 is a flowchart showing a procedure of a second provisional compression parameter generation processing in the first embodiment of the present invention.

The second provisional compression parameter generation processing will then be described with reference to FIGS. 2, 3, and 7. FIG. 7 is a flowchart showing a procedure of the second provisional compression parameter generation processing. The second provisional compression parameter generation processing is carried out by the second compression parameter generation unit 27C2. In the second provisional compression parameter generation processing, the second compression parameter generation unit 27C2 first acquires a maximum V2 of the data quantities in the plurality of compressed portions generated from single image data and stored in the compressed data storage unit 24A (step S41).

The second compression parameter generation unit 27C2 specifies a second target data quantity T2 based on the storage capacity of the compressed data storage unit 24A (step S42). The second target data quantity T2 is specified to be smaller than the storage capacity of the compressed data storage unit 24A, for example, by subtracting a predetermined value from the storage capacity of the compressed data storage unit 24A or multiplying the storage capacity of the compressed data storage unit 24A by a predetermined coefficient smaller than 1.

The second compression parameter generation unit 27C2 next generates the second provisional compression parameter Q2 by performing second computation of calculating the compression parameter for compressing the image data in such a way that the maximum V2 is smaller than or equal to the second target data quantity T2 (step S43). The second computation is expressed, for example, by Equation (2) below.

$$Q2(n) = Q3(n-1) + A2*(V2-T2)/T2 \quad (2)$$

In Equation (2), $Q2(n)$ represents the second provisional compression parameter Q2 calculated n-th time when the first setting processing (step S19A) shown in FIG. 4 is carried out n times (n is integer greater than or equal to 1). $Q3(n-1)$ represents the setting parameter Q3 set (n-1)-th time, as described above. The second compression parameter generation unit 27C2 reads $Q3(n-1)$ from the storage unit 24 and calculates $Q2(n)$. A2 is a positive integer.

A second provisional compression parameter Q2(1) calculated first is calculated by using a predetermined constant in place of $Q3(n-1)$ in Equation (2). The predetermined constant may be the initial value Qi.

The reason why using the second provisional compression parameter Q2 calculated by using Equation (2) allows the compression processing to be carried out so that the maximum V2 is smaller than or equal to the second target data quantity T2 is as follows: In other words, the maximum V2 corresponds to the maximum of the data quantities in the plurality of compressed portions in the case where $Q3(n-1)$ is used as the compression parameter. As will be seen from Equation (2), when the maximum V2 is greater than the second target data quantity T2, $Q2(n)$ is greater than $Q3(n-1)$, resulting in a decrease in the maximum of the data quantities in the plurality of compressed portions in a case where $Q2(n)$ is used as the compression parameter. Appropriate selection of a value of A2 allows the maximum of the data quantities in the plurality of compressed portions in the case where $Q2(n)$ is used as the compression parameter to be smaller than or equal to the second target data quantity T2. In the present embodiment, the second provisional compression parameter Q2, which is a compression parameter that allows the compression processing to be carried out so that the maximum V2 is smaller than or equal to the second target data quantity T2, is generated as described above.

As will be seen from Equation (2), when the maximum V2 is smaller than the second target data quantity T2, $Q2(n)$ is smaller than $Q3(n-1)$, resulting in an increase in the maximum of the data quantities in the plurality of compressed portions in the case where $Q2(n)$ is used as the compression parameter. As the value of A2, a value that does not cause the maximum of the data quantities in the plurality of compressed portions in the case where $Q2(n)$ is used as the compression parameter is not too large is selected. As will be seen from Equation (2), when the maximum V2 is equal to the second target data quantity T2, $Q2(n)$ is equal to $Q3(n-1)$.

In the second provisional compression parameter generation processing, the second compression parameter generation unit 27C2 then outputs the second provisional compression parameter Q2 to the compression parameter judgement unit 27C3 (step S44). The second provisional compression parameter generation processing thus ends.

FIG. 7 shows an example in which the second target data quantity T2 is specified whenever the second provisional compression parameter generation processing is carried out. In the present embodiment, the storage capacity of the compressed data storage unit 24A, which specifies the second target data quantity T2, is fixed. Therefore, in the present embodiment, the processing of specifying the second target data quantity T2 (step S42) may be omitted.

(Compression Parameter Selection Processing)

The compression parameter selection processing will next be described with reference to FIG. 3. The compression parameter selection processing is carried out by the compression parameter judgement unit 27C3. In the compression parameter selection processing, the compression parameter judgement unit 27C3 compares the first provisional compression parameter Q1 generated by the first compression parameter generation unit 27C1 with the second provisional compression parameter Q2 generated by the second compression parameter generation unit 27C2. The compression parameter judgement unit 27C3 then selects a parameter that causes the data quantity after the compression decreases out of the first provisional compression parameter Q1 and the second provisional compression parameter Q2 and sets the selected parameter as the setting parameter Q3. The compression parameter selection processing thus ends.

As described above, in the present embodiment, the compression parameter Q is specified so that the data quantity after the compression decreases as the value of the compression parameter Q increases. The data quantity after the compression therefore decreases as the value of each of the first provisional compression parameter Q1 and the second provisional compression parameter Q2 increases. Therefore, in the present embodiment, the comparison performed by the compression parameter judgement unit 27C3 is performed by comparing the value of the first provisional compression parameter Q1 with the value of the second provisional compression parameter Q2. Further, in the present embodiment, out of the first provisional compression parameter Q1 and the second provisional compression parameter Q2, a parameter having a larger value is selected as the setting parameter Q3.

The above description has been made of the case where the compression parameter generation processing includes the first provisional compression parameter generation processing, the second provisional compression parameter generation processing, and the compression parameter selection processing. However, the compression parameter generation processing in the present embodiment is not limited to the case described above. For example, the compression parameter generation processing may include only the same processing as the first provisional compression parameter generation processing. In this case, the parameter setting unit 27C sets a compression parameter generated by the same method for generating the first provisional compression parameter Q1 as the setting parameter Q3.

(Effects and Advantages)

Effects and advantages of the endoscope apparatus 1 according to the present embodiment will next be described. In the present embodiment, the image pickup of an object and the generation of image data are continuously performed multiple times, and the judgement processing (step S18 in FIG. 4) is carried out whenever image data is generated. The compression parameter is determined based on a result of the judgement processing. Therefore, according to the present embodiment, continuation of a state in which no image of an object is displayed on the monitor 4 can be avoided. The aforementioned advantage will be described below in comparison with an endoscope apparatus according to Comparative Example.

The endoscope apparatus according to Comparative Example is not provided with the information quantity detection unit 27A or the judgement unit 27B in the present embodiment. In Comparative Example, whenever the image pickup unit 21 generates image data, the setting parameter Q3 is set based only on compressed data corresponding to the image data. The compression parameter used in the compression processing control unit 23 is updated by the setting parameter Q3 whenever the setting parameter Q3 is set. Other components of the endoscope apparatus according to Comparative Example are the same as the components of the endoscope apparatus 1 according to the present embodiment.

Figure 8:
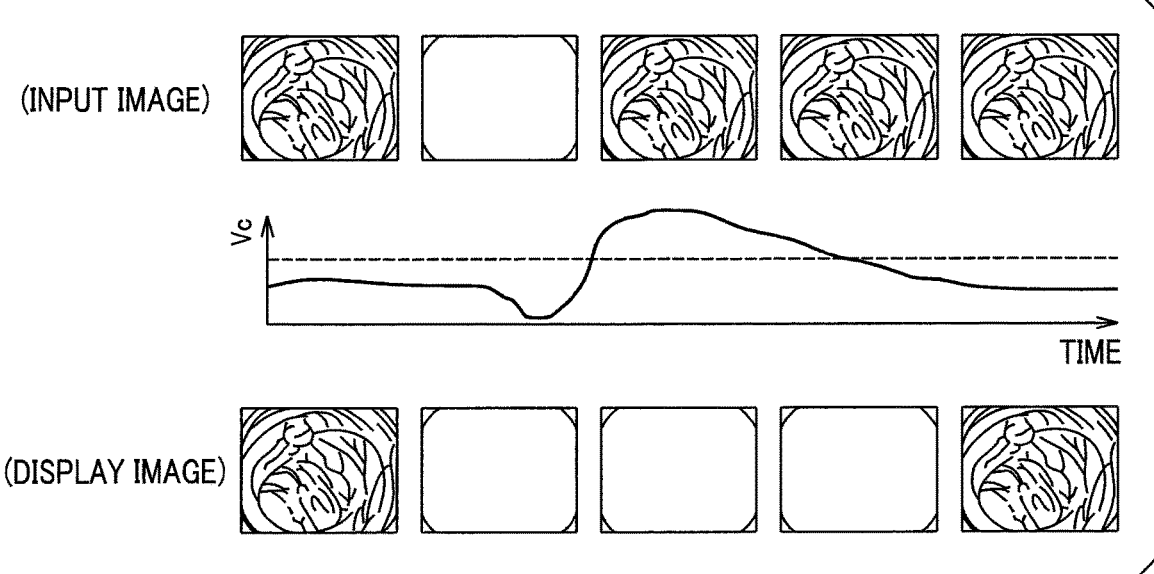
FIG. 8 is a descriptive diagram diagrammatically showing input images, display images, and a data quantity of compressed data in an endoscope apparatus according to Comparable Example.

FIG. 8 diagrammatically shows images corresponding to compressed data inputted to the parameter setting unit 27C (expressed as input image in FIG. 8), display images displayed on the monitor 4, and a change in a data quantity Vc of the compressed data in the endoscope apparatus according to Comparable Example. In FIG. 8, a broken line represents the transferable data quantity. FIG. 8 shows input images and display images arranged at predetermined intervals. In FIG. 8, input images and display images having undergone the same image data processing as the image data processing shown in FIGS. 4 and 5 based on image data corresponding to the input images are arranged next to each other in a vertical direction in FIG. 8.

In FIG. 8, a left-end input image and output image are images of an object having been normally picked up that have the compressed data quantity Vc smaller than or equal to the transferable data quantity. Second input image and display image counted from the left end are images of the object not having been normally picked up. FIG. 8 shows halation images as the images of the object not having been normally picked up.

In the Comparable Example, when compressed data is generated by compressing small information quantity image data on the object, the data quantity Vc of the compressed data is smaller than the data quantity Vc based on the normally picked-up image data. In particular, when the object cannot be picked up, such as halation images, the data quantity Vc is extremely small. As a result, the setting parameter Q3 set based on the data quantity Vc and the compression parameter updated by the setting parameter Q3 are extremely small, and the data quantity Vc of compressed data generated by using the compression parameter is undesirably greater than the transferable data quantity. Therefore, even when a state in which the object can be normally picked up is restored, such as a state in which third input image and display image counted from the left end in FIG. 8 are produced, the compressed data cannot be transmitted, so that no image of the object can be displayed on the monitor 4.

In Comparable Example, once the setting parameter Q3 is extremely small, a certain period is required for the setting parameter Q3 to return to an appropriate value. It is therefore necessary to provide a certain period that allows the data quantity Vc to be smaller than or equal to the transferable data quantity, as shown in FIG. 8. As described above, when the state in which the data quantity Vc is greater than the transferable data quantity continues, the state in which no image of the object is displayed on the monitor 4 undesirably continues.

In contrast, in the present embodiment, the compression parameter Q is determined based on the data quantity of compressed data and a judgement result from the judgement unit 27B. In the present embodiment, in particular, the compression parameter Q is updated by the setting parameter Q3 when the judgement value is greater than or equal to the predetermined threshold and the compression parameter is not updated when the judgement value is smaller than the predetermined threshold. In other words, in the present embodiment, when image data having a small object information quantity is generated, the compressed data is generated by using the compression parameter generated when normally picked up image data is generated. Therefore, according to the present embodiment, when image data having a small object information quantity is generated, a situation in which the compression parameter is extremely small can be avoided.

Figure 9:
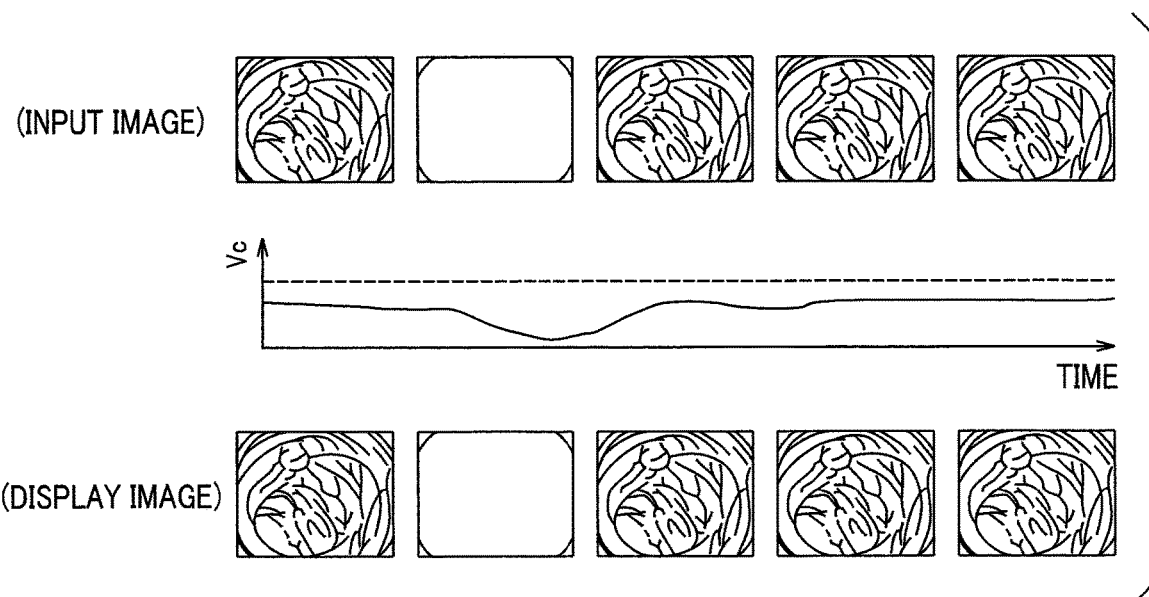
FIG. 9 is a descriptive diagram diagrammatically showing the input images, the display images, and the data quantity of the compressed data in the endoscope apparatus according to the first embodiment of the present invention.

FIG. 9 diagrammatically shows images corresponding to compressed data inputted to the parameter setting unit 27C (expressed as input image in FIG. 9), display images displayed on the monitor 4, and a change in the data quantity Vc of the compressed data in the endoscope apparatus 1 according to the present embodiment. In FIG. 9, a broken line represents the transferable data quantity. A method for arranging the input images and the display images is the same as the method used in FIG. 8.

Also in the present embodiment, when an object cannot be normally picked up, like a second input image and display image counted from the left end in FIG. 9, the monitor 4 displays no image of the object. However, in the present embodiment when image data having a small object information quantity is generated, compressed data is generated by using the compression parameter generated when normally picked up image data is generated, as described above. Therefore, according to the present embodiment, the situation in which the data quantity Vc is greater than the transferable data quantity can be avoided, and when the state in which the object can be normally picked up is restored, like a third input image and display image counted from the left end in FIG. 9, an image of the object can be displayed on the monitor 4. Therefore, according to the present embodiment, continuation of the state in which no image of an object is displayed on the monitor 4 can be avoided.

In the present embodiment, a display image is determined based on a result of the judgement processing carried out by the judgement unit 27B, and when a judgement value in the judgement processing is greater than or equal to a predetermined threshold, the display image is an image corresponding to image data generated when the current judgement processing is carried out. In the present embodiment, even when an object cannot be normally picked up, determining the compression parameter as described above can prevent the display image to be affected by the image not having been normally picked up. Therefore, in the present embodiment, when the state in which the object can be normally picked up is restored, determining the display image as described above allows an image of the object to be displayed on the monitor 4. The present embodiment can therefore prevent continuation of the state in which no image of an object is displayed on the monitor 4.

Note that in the present embodiment, when an object cannot be normally picked up, the monitor 4 displays no image of the object. The present embodiment therefore allows the user to be notified that the object has not been normally picked up. Note that as will be described later as a modification, when an object cannot be normally picked up, the display image can be an image picked up when the object is normally picked up, as in the case of the compression parameter. In other words, when a judgement value in the judgement processing is equal to the predetermined threshold, the display image may be an image corresponding to image data generated when the current judgement processing is carried out or an image determined based on a result of a preceding judgement processing.

If the information quantity detection unit 27A, the judgement unit 27B, and the parameter setting unit 27C are provided in the processor 3, and when the transferable data quantity decreases due, for example, to deterioration of the wireless communication environment, the image quantity decreases, resulting in problematic situations in which accuracy of detection of the object information quantity decreases, the object information quantity cannot be detected, and the setting parameter Q3 cannot be set. In contrast, in the present embodiment, the information quantity detection unit 27A, the judgement unit 27B, and the parameter setting unit 27C are provided in the endoscope 2. The present embodiment can therefore avoid occurrence of the problems described above.

In the present embodiment, the compressed data storage unit 24A successively stores a plurality of compressed portions generated from single image data. If the quantity of data on one or more of the plurality of compressed portions is greater than the storage capacity of the compressed data storage unit 24A, the compressed data cannot be transmitted, and the monitor 4 therefore cannot display an image of the object. In contrast, in the present embodiment, to set the setting parameter Q3, the first provisional compression parameter Q1 and the second provisional compression parameter Q2 are generated. Therefore, according to the present embodiment, even when either the first provisional compression parameter Q1 or the second provisional compression parameter Q2 is set as the setting parameter Q3, the calculated data quantity V1 (compressed data quantity) is smaller than or equal to the first target data quantity T1, whereby the compression processing can be carried out so that the maximum V2 of the data quantities in the plurality of compressed portions is smaller than or equal to the second target data quantity T2. As a result, according to the present embodiment, the compression processing can be carried out so that the data quantity of the compressed data is smaller than or equal to the transferable data quantity and the data quantity in each of the plurality of compressed portions is smaller than or equal to the storage capacity of the storage unit 24A. The present embodiment can therefore avoid disruption of compressed data transmission.

(Modifications)

A modification of the image data processing procedure in the endoscope 2 and a modification of the image data processing procedure in the processor 3 will next be described.

Figure 10:
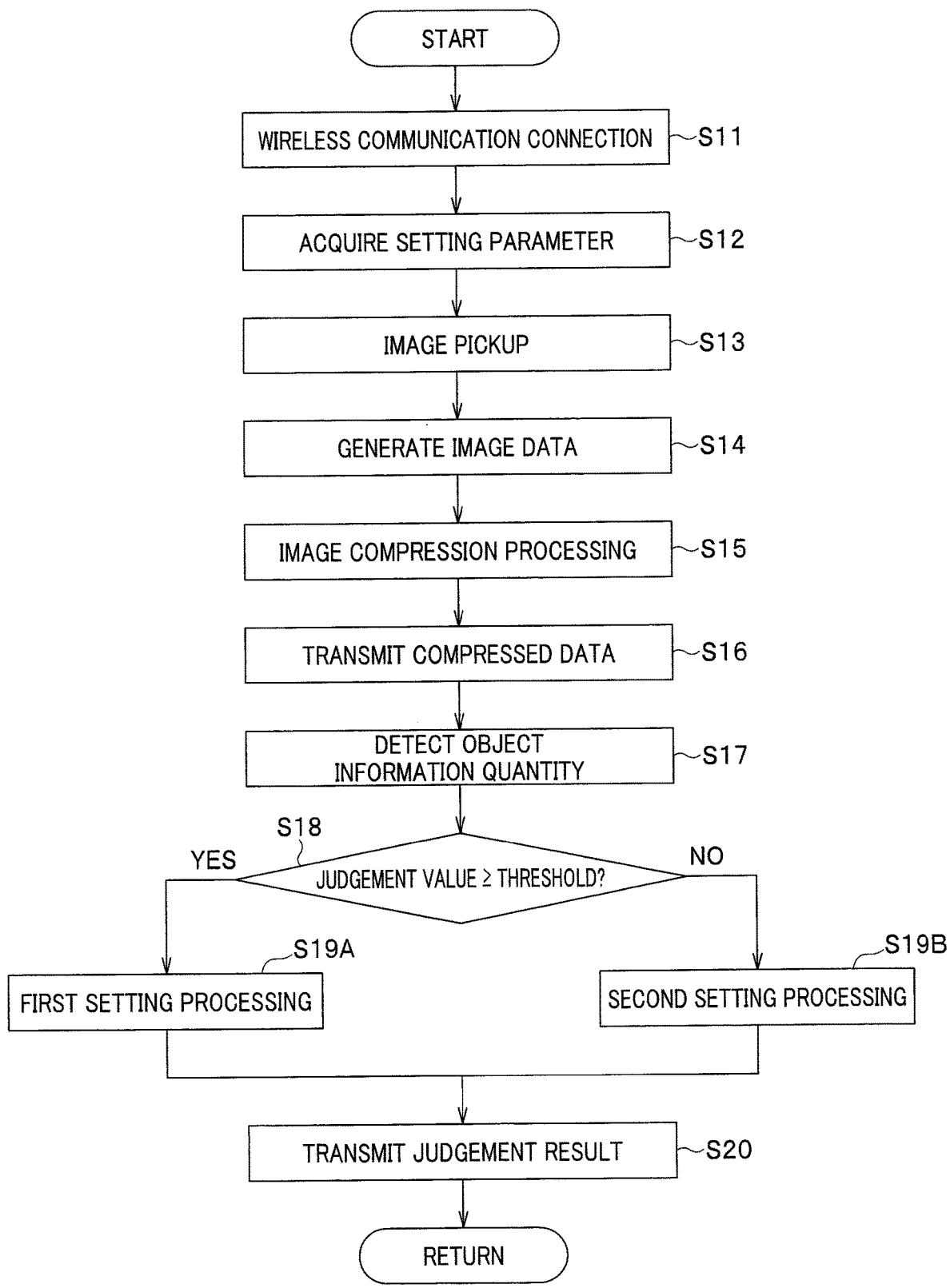
FIG. 10 is a flowchart showing a modification of the image data processing procedure in the endoscope shown in FIG. 2.

The modification of the image data processing procedure in the endoscope 2 will first be described with reference to FIGS. 2, 3, and 10. FIG. 10 is a flowchart showing the modification of the image data processing procedure in the endoscope 2. In the modification, the image data processing procedure to the procedure of carrying out the first setting processing (step S19A) and the procedure of carrying out the second setting processing (step S19B) is the same as the image data processing procedure in the endoscope 2 shown in FIG. 4.

In the modification, the endoscope control unit 22 then controls the first wireless communication unit 25 to transmit a judgement result provided by the judgement unit 27B and stored in the storage unit 24 to the processor 3 (step S20). When the operation signal based on the user's operation instructing end of the image pickup processing is not inputted to the endoscope control unit 22, the endoscope control unit 22 returns to step S11, whereas when the operation signal described above is inputted to the endoscope control unit 22, the endoscope control unit 22 terminates the image data processing in the endoscope 2.

Figure 11:
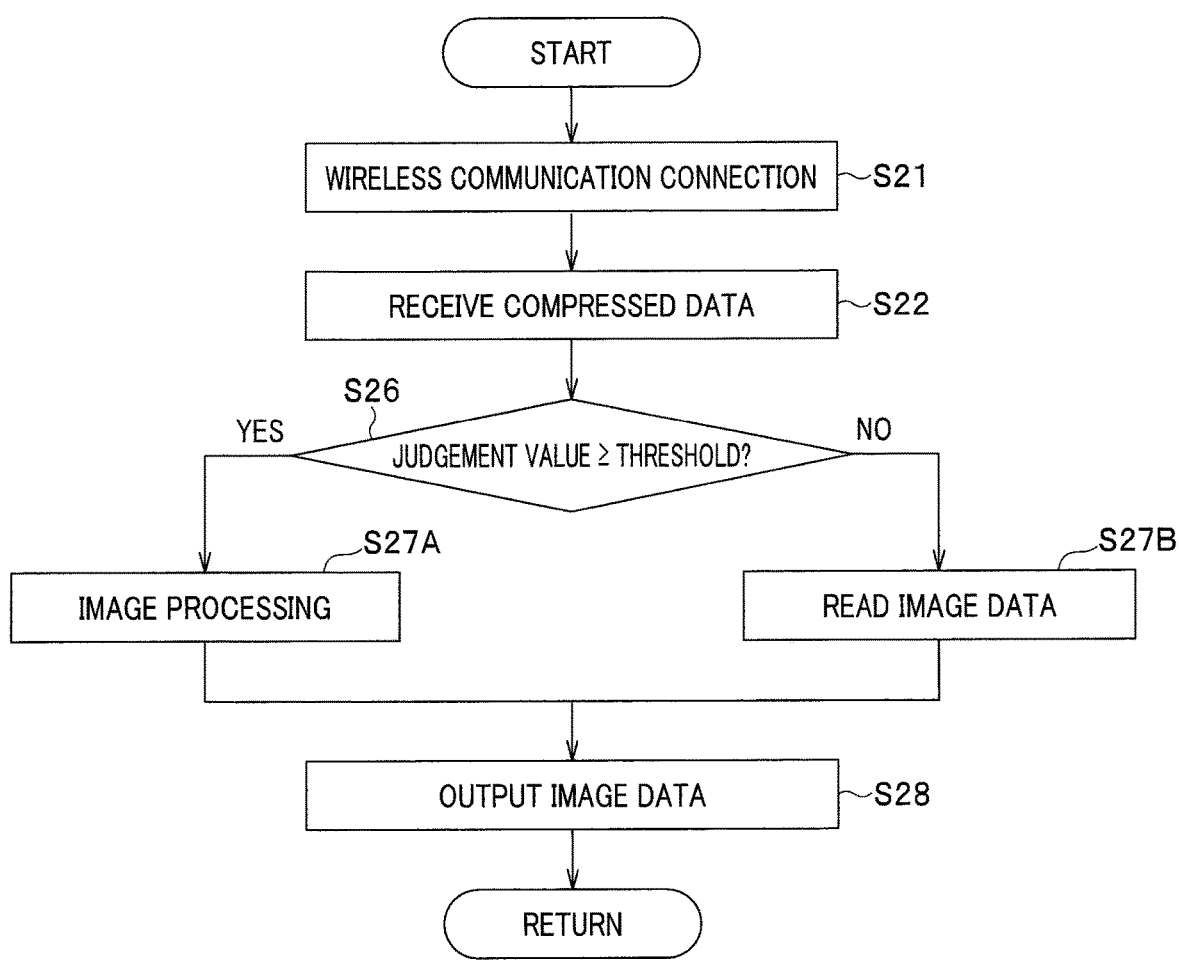
FIG. 11 is a flowchart showing a modification of the image data processing procedure in the processor shown in FIG. 2.

The modification of the image data processing procedure in the processor 3 will next be described with reference to FIGS. 2, 3, and 11. FIG. 11 is a flowchart showing the modification of the image data processing procedure in the processor 3. The image data processing procedure to the processing of receiving transmitted compressed data (step S22) is the same as the image data processing procedure in the processor 3 shown in FIG. 5, as shown in FIG. 11.

In the modification, the processor control unit 31 then controls the second wireless communication unit 32A to receive the judgement result provided by the judgement unit 27B and transmitted by the first wireless communication unit 25 (step S25). The received judgement result is stored in the storage unit 36.

The image processing unit 33 then reads the judgement result from the storage unit 36 and carries out a determination processing of determining a display image based on the judgement result (step S26). When the judgement value is greater than or equal to the predetermined threshold (YES), it can be judged that the object information quantity is sufficient, that is, the object has been normally picked up. In this case, the image processing unit 33 determines as the display image an image corresponding to image data generated when a judgement processing using the judgement value (judgement processing carried out N-th time) is carried out.

When the judgement value is smaller than the predetermined threshold (NO), it can be judged that the object information quantity is insufficient, that is, the object has not been normally picked up. In this case, the image processing unit 33 determines as the display image an image determined based on a result of a judgement processing preceding the judgement processing using the judgement value (judgement processing carried out (N−1)-th time). When a judgement value in the preceding judgement processing is greater than or equal to the predetermined threshold, the image processing unit 33 determines as the display image an image corresponding to image data generated when the preceding judgement processing is carried out. When the judgement value in the preceding judgement processing is smaller than the predetermined threshold, the image processing unit 33 determines as the display image an image corresponding to image data generated when a judgement processing that has been carried out before the preceding judgement processing and provides a judgement value greater than or equal to the predetermined threshold is carried out.

When the judgement value is greater than or equal to the predetermined threshold in step S26 (YES), the image processing unit 33 then generates image data (step S27A) decompressed by the same image processing in step S23 in FIG. 5. In the modification, the image processing unit 33 outputs the decompressed image data to the storage unit 36. The storage unit 36 stores the decompressed image data.

When the judgement value is smaller than the predetermined threshold in step S26 (NO), the image processing unit 33 reads image data corresponding to the determined display image from the storage unit 36 (step S27B). Noted that, instead of reading the image data, the image processing unit 33 may read compressed data generated from the image data corresponding to the determined display image and decompresses the compressed data to generate decompressed image data.

In the image data processing in the processor 3, after step S27A or step S27B, the image processing unit 33 outputs the decompressed image data or the read image data to the monitor 4 (step S28). When the operation signal based on the user's operation instructing end of the image pickup processing is not inputted to the processor control unit 31, the processor control unit 31 returns to step S21, whereas when the operation signal described above is inputted to the processor control unit 31, the processor control unit 31 terminates the image data processing in the processor 3.

In the modification, when the judgement value is smaller than the predetermined threshold, the image processing unit 33 determines as the display image an image determined based on the result of the judgement processing preceding the judgement processing using the judgement value. In other words, in the modification, when image data having a small object information quantity is generated, an image corresponding to image data generated when the object is normally picked up is used as the display image. The monitor 4 can therefore keep displaying an image of the object in the modification.

In the modification, the processing of transmitting the compressed data (step S16 in FIG. 10) may be carried out between the first setting processing (step S19A in FIG. 10) and the processing of transmitting a judgement result (step S20 in FIG. 10). In this case, when the judgement value in the judgement processing (step S18 in FIG. 10) is smaller than the predetermined threshold, no compressed data is transmitted.

The endoscope apparatus 1 may be configured so that when image data having a small object information quantity is generated, an image corresponding to the image data having a small object information quantity and an image corresponding to image data generated when the object is normally picked up can be switched as the display image from one to the other.

Second Embodiment

Figure 12:
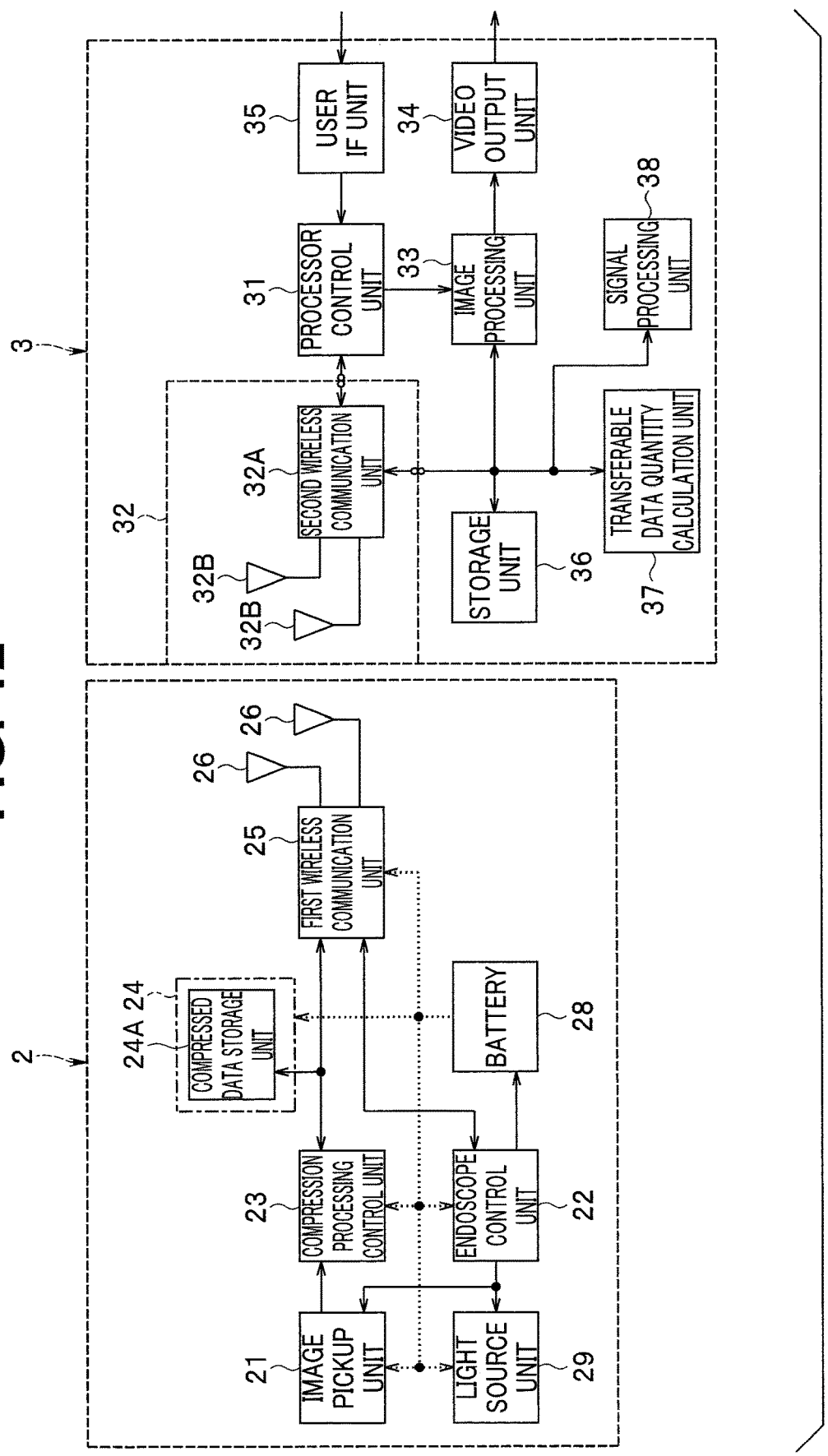
FIG. 12 is a functional block diagram showing configurations of the endoscope and the processor of an endoscope apparatus according to a second embodiment of the present invention.

An endoscope apparatus according to a second embodiment of the present invention will next be described. A difference in configuration between the endoscope apparatus 1 according to the present embodiment and the endoscope apparatus 1 according to the first embodiment will first be described with reference to FIG. 12. FIG. 12 is a functional block diagram showing the configurations of the endoscope 2 and the processor 3.

In the present embodiment, the endoscope 2 is not provided with the signal processing unit 27 in the first embodiment. Instead, the processor 3 includes a signal processing unit 38. The signal processing unit 38 is configured of a processor including hardware, for example, a CPU or a DSP.

Figure 13:
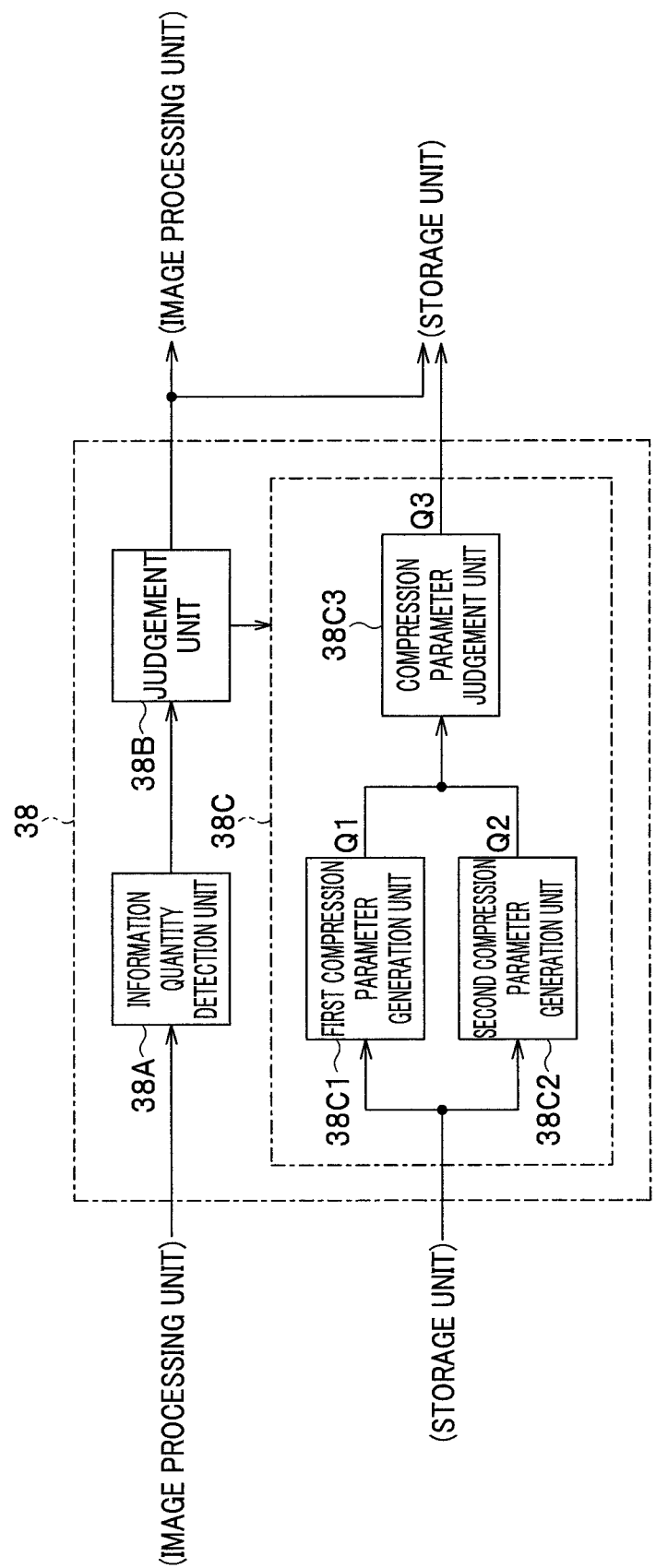
FIG. 13 is a functional block diagram showing a configuration of a signal processing unit in the second embodiment of the present invention.

FIG. 13 shows a configuration of the signal processing unit 38. The configuration of the signal processing unit 38 is the same as the configuration of the signal processing unit 27 in the first embodiment. In other words, the signal processing unit 38 includes an information quantity detection unit 38A, a judgement unit 38B, and a parameter setting unit 38C. The parameter setting unit 38C includes a first compression parameter generation unit 38C1, a second compression parameter generation unit 38C2, and a compression parameter judgement unit 38C3.

Decompressed image data generated by the image processing unit 33 is inputted to the information quantity detection unit 38A. The information quantity detection unit 38A detects the object information quantity contained in the image data and outputs the object information quantity to the judgement unit 38B. The judgement unit 38B performs a predetermined judgement processing based on the object information quantity and outputs a judgement result to the storage unit 36 and the parameter setting unit 38C. The storage unit 36 stores the judgement result. The method for detecting the information quantity and the contents of the judgement processing are the same as the method and the contents in the first embodiment.

The parameter setting unit 38C sets a compression parameter used in the compression processing control unit 23 based on the judgement result from the judgement unit 38B and the compressed data stored in the storage unit 36. The first compression parameter generation unit 38C1 and the second compression parameter generation unit 38C2 are each configured to be capable of acquiring the data quantity of the compressed data stored in the storage unit 36. The first compression parameter generation unit 38C1 generates the first provisional compression parameter Q1 and outputs the first provisional compression parameter Q1 to the compression parameter judgement unit 38C3. The second compression parameter generation unit 38C2 generates the second provisional compression parameter Q2 and outputs the second provisional compression parameter Q2 to the compression parameter judgement unit 38C3.

The compression parameter judgement unit 38C3 compares the first provisional compression parameter Q1 with the second provisional compression parameter Q2, selects one of the two provisional compression parameters, and sets the selected compression parameter as the setting parameter Q3. The compression parameter judgement unit 38C3 outputs the setting parameter Q3 to the compression processing control unit 23 in the endoscope 2 via the wireless communication between the endoscope 2 and the processor 3 and outputs the selected compression parameter to the storage unit 36. The storage unit 36 stores the selected compression parameter. The method for setting the setting parameter Q3 is the same as the method in the first embodiment.

In the present embodiment, signals transmitted and received by the first wireless communication unit 25 of the endoscope 2 and the second wireless communication unit 32A of the wireless receiver 32 of the processor 3 contain the compressed data stored in the compressed data storage unit 24A and the setting parameter Q3 stored in the storage unit 36.

(Image Data Processing in Endoscope)

Figure 14:
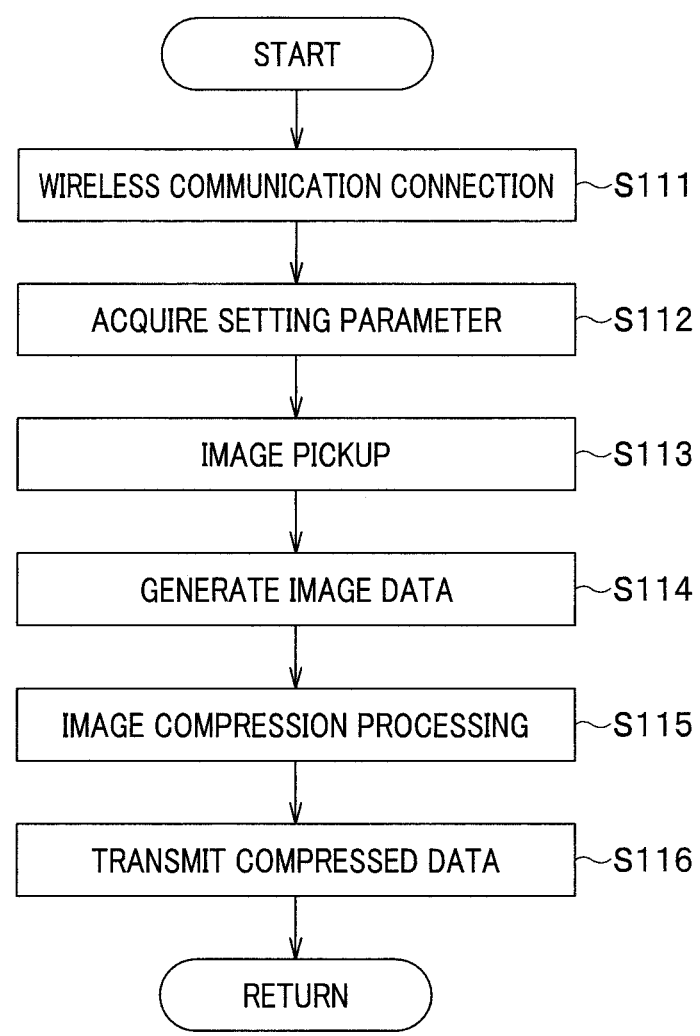
FIG. 14 is a flowchart showing an image data processing procedure in the endoscope shown in FIG. 12.

The image data processing procedure in the endoscope 2 according to the present embodiment will next be described with reference to FIGS. 12 and 14. FIG. 14 is a flowchart showing the image data processing procedure in the endoscope 2. The image data processing in the endoscope 2 according to the present embodiment includes a compression processing in the compression processing control unit 23.

The image data processing in the endoscope 2 according to the present embodiment is performed by the endoscope control unit 22 and the compression processing control unit 23. Conditions of the start and the end of the image data processing in the endoscope 2 are the same as the conditions in the first embodiment.

In the image data processing in the endoscope 2, the endoscope control unit 22 first establishes wireless communication connection between the endoscope 2 and the processor 3 (step S111). The contents of step S111 are the same as the contents of step S11 in FIG. 4 in the first embodiment.

The processing of acquiring the setting parameter Q3 is then carried out (step S112). In the process, the endoscope control unit 22 first controls the first wireless communication unit 25 to receive the setting parameter Q3 transmitted by the second wireless communication unit 32A. The received setting parameter Q3 is stored in the storage unit 24. The compression processing control unit 23 then reads the setting parameter Q3 from the storage unit 24. Note that in the image data processing performed first, the compression processing control unit 23 acquires the initial value Qi of the compression parameter in place of the setting parameter Q3. The initial value Qi may be a set value inputted to the user IF unit 35 or a set value stored in the storage unit 24.

The endoscope control unit 22 then controls the image pickup unit 21 to pick up an image of an object to generate image data by using, as power source, electric power supplied from the battery 28 (steps S113 and S114). The compression processing control unit 23 then carries out the image compression processing of compressing the image data to generate compressed data (step S115). The compressed data is stored in the compressed data storage unit 24A. The endoscope control unit 22 then controls the first wireless communication unit 25 to transmit the compressed data stored in the compressed data storage unit 24A to the processor 3 (step S116). The contents of steps S113 to S116 are the same as the contents of steps S13 to S16 in FIG. 4 in the first embodiment.

When the operation signal based on the user's operation instructing end of the image pickup processing is not inputted to the endoscope control unit 22, the endoscope control unit 22 returns to step S111, whereas when the operation signal described above is inputted to the endoscope control unit 22, the endoscope control unit 22 terminates the image data processing in the endoscope 2.

(Image Data Processing in Processor)

Figure 15:
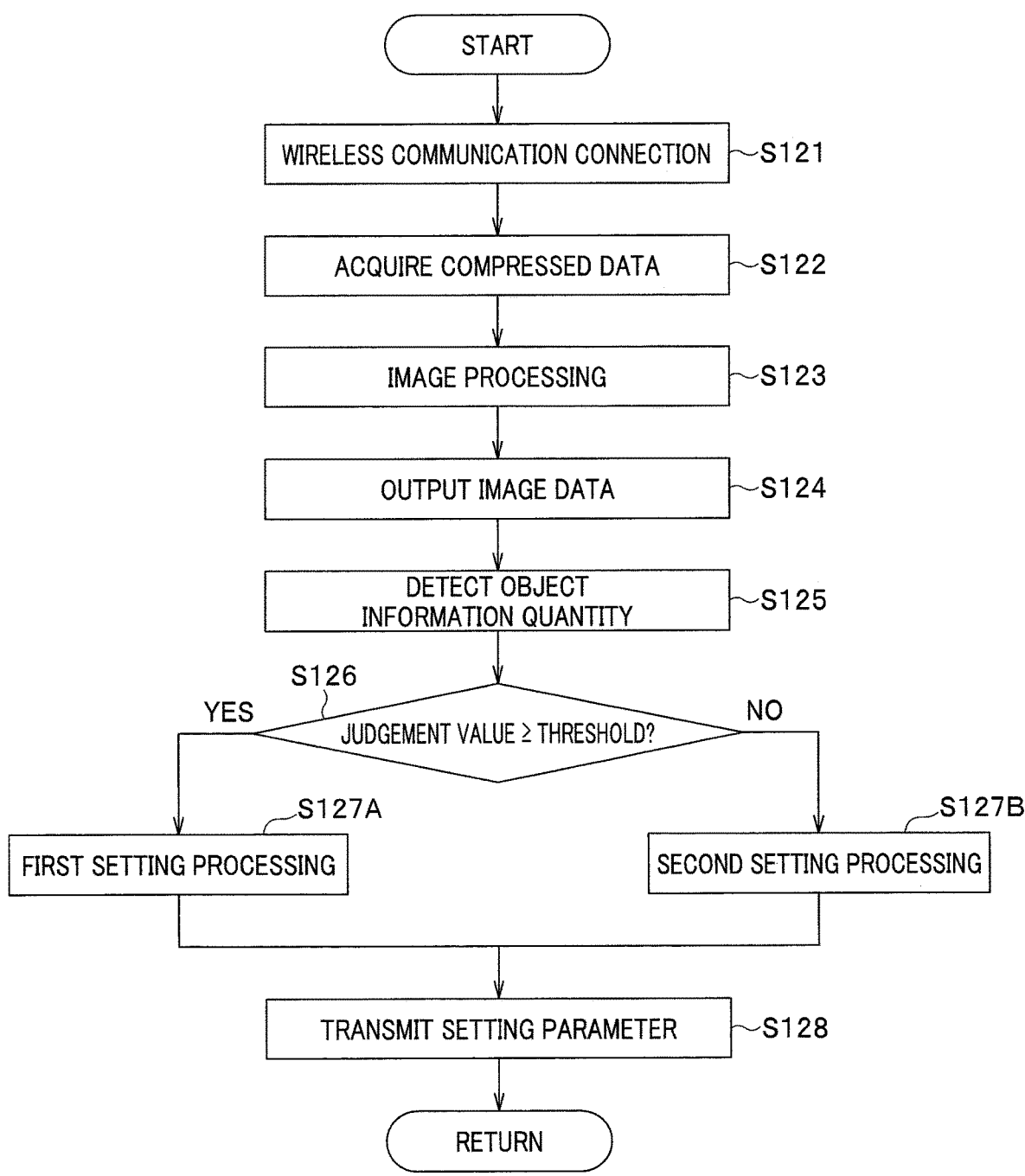
FIG. 15 is a flowchart showing an image data processing procedure in the processor shown in FIG. 12.

The image data processing procedure in the processor 3 in the present embodiment will next be described with reference to FIGS. 12, 13 and 15. FIG. 15 is a flowchart showing the image data processing procedure in the processor 3. The image data processing in the processor 3 includes the processing of detecting the object information quantity in the information quantity detection unit 38A, a judgement processing in the judgement unit 38B, and a parameter setting processing in the parameter setting unit 38C.

The image data processing in the processor 3 in the present embodiment is carried out by the processor control unit 31, the image processing unit 33, and the signal processing unit 38. The conditions of the start and the end of the image data processing in the processor 3 are the same as the conditions in the first embodiment.

In the image data processing in the processor 3, the processor control unit 31 first establishes wireless communication connection between the endoscope 2 and the processor 3 (step S121). The processor control unit 31 then controls the second wireless communication unit 32A to receive the compressed data, that is, the plurality of compressed portions transmitted by the first wireless communication unit 25 (step S122). The image processing unit 33 then reads the compressed data from the storage unit 36 and performs predetermined image processing on the compressed data (step S123). The contents of steps S121 to S123 are the same as the contents of steps S21 to S23 in FIG. 5 in the first embodiment.

The image processing unit 33 then outputs the decompressed image data to the monitor 4 and the information quantity detection unit 38A of the signal processing unit 38 (step S124).

The information quantity detection unit 38A of the signal processing unit 38 carries out the processing of detecting the object information quantity contained in the decompressed image data (step S125). The contents of step S125 are the same as the contents of step S17 in FIG. 4 in the first embodiment.

The judgement unit 38B of the signal processing unit 38 then carries out the judgement processing of judging whether or not a judgement value relating to the object information quantity detected by the information quantity detection unit 38A is smaller than a predetermined threshold (step S126). The judgement unit 38B outputs a judgement result to the storage unit 36 and the parameter setting unit 38C. As described in the first embodiment, when the judgement value is greater than or equal to the predetermined threshold (YES), it can be judged that the object information quantity is sufficient, that is, the object has been normally picked up. On the other hand, when the judgement value is smaller than the predetermined threshold (NO) in the judgement processing, it can be judged that the object information quantity is insufficient, that is, the object has not been normally picked up.

The parameter setting unit 38C of the signal processing unit 38 then carries out the parameter setting processing based on the judgement result from the judgement unit 38B. When the judgement value is greater than or equal to the predetermined threshold (YES), the parameter setting unit 38C carries out the first setting processing (step S127A), and when the judgement value is smaller than the predetermined threshold (NO), the parameter setting unit 38C carries out the second setting processing (step S127B). The contents of the first and second setting processings are the same as the contents in the first embodiment.

In the image data processing in the processor 3, after the step S127A or S127B, the processor control unit 31 controls the second wireless communication unit 32A to transmit the setting parameter Q3 stored in the storage unit 36 to the endoscope 2 (step S128). When the operation signal based on the user's operation instructing end of the image pickup processing is not inputted to the processor control unit 31, the processor control unit 31 returns to step S121, whereas when the operation signal described above is inputted to the processor control unit 31, the processor control unit 31 terminates the image data processing in the processor 3.

(Effects and Advantages)

In the present embodiment, the processor 3 is provided with the signal processing unit 38 in place of the signal processing unit 27 provided in the endoscope 2. Therefore, according to the present embodiment, the amount of computation processing in the endoscope 2 is reduced, whereby the electric power consumed by the endoscope 2 can be reduced.

Note that when the judgement value in the judgement processing is smaller than the predetermined threshold, the image processing unit 33 may determine as the display image an image determined based on a result of a preceding judgement processing, as in the modification of the first embodiment. Other components, effects, and advantages in the present embodiment are the same as the other components, effects, and advantages in the first embodiment.

The present invention is not limited to the embodiments described above, and a variety of changes, improvements, and other modifications can be made thereto to the extent that the changes, improvements, and other modifications do not change the gist of the present invention. For example, the endoscope apparatus according to the present invention may be an endoscope apparatus having a configuration in which the endoscope and the processor are connected to each other via a universal cable. In the thus configured endoscope apparatus, the transmission path along which image data is transmitted is entirely configured of a wired transmission path and includes no wireless transmission path.

In the first embodiment, the parameter setting unit 27C may be provided in the processor 3. Therefore, the amount of computation processing in the endoscope 2 can be reduced, whereby the electric power consumed by the endoscope 2 can be reduced, as compared with the case where the parameter setting unit 27C is provided in the endoscope 2.

What is claimed is:

1. An image data processing device comprising:
a processor configured to:
carry out a compression processing of compressing image data, stored in a storage device, by using a compression parameter that is a value that specifies a data quantity after compression to generate compressed data;
detect a quantity of information on an object contained in the compressed image data;
calculate a judgment value corresponding to the quantity of information;
carry out a comparison processing of comparing the judgement value with a predetermined threshold; and
determine whether or not to update the compression parameter based on a result of the comparison processing,
wherein assuming that transferable data quantity is a quantity of data transferable along a transmission path along which the image data is transmitted, the processor is configured to update the compression parameter by carrying out a generation processing including first computation of calculating a compression parameter for compressing the image data in such a way that a calculated data quantity relating to a data quantity of the compressed data is smaller than or equal to a first target data quantity specified based on the transferable data quantity,
wherein the processor is configured to:
carry out compression processing on the image data by using the compression parameter for each of a plurality of unit areas of the image data; and
generate a plurality of compressed portions as the compressed data from the image data that is single image data,
wherein the storage device has a predetermined size storage capacity and successively stores the plurality of compressed portions, and
wherein the generation processing further includes second computation of calculating a compression parameter for compressing the image data in such a way that a maximum of data quantities of the plurality of compressed portions is smaller than or equal to a second target data quantity specified based on the storage capacity, and processing of comparing the compression parameter calculated by the first computation with the compression parameter calculated by the second computation and selecting a parameter that causes the data quantity after compression to decrease.

2. The image data processing device according to claim 1, wherein the processor is configured to:
in response to the result of the comparison processing being that the judgment value is equal to or greater than the predetermined threshold,
determine to update the compression parameter; and
update the compression parameter to a setting parameter that is the compression parameter set by the processor; and
in response to the result of the comparison processing being that the judgment value is less than the predetermined threshold, determine not to update the compression parameter.

3. The image data processing device according to claim 2, wherein the processor is configured to, in response to the result of the comparison processing being that the judgment value is equal to or greater than the predetermined threshold, update the compression parameter to the setting parameter based on the compressed data corresponding to the image data at the current time point.

4. The image data processing device according to claim 3, wherein the processor is configured to:
in response to the result of the comparison processing being that the judgment value is equal to or greater than the predetermined threshold, control the storage device to store the updated compression parameter; and
in response to the result of the comparison processing being that the judgment value is less than the predetermined threshold, set the compression parameter stored in the storage device as the setting parameter.

5. The image data processing device according to claim 1, wherein the quantity of information is specified based on color information contained in the image data.

6. The image data processing device according to claim 1, wherein the quantity of information is specified based on a resolution in the image data.

7. The image data processing device according to claim 1, wherein the quantity of information is specified based on the data quantity of the compressed data.

8. The image data processing device according to claim 1, wherein the judgement value is a difference between the quantity of information detected at a current time point and a quantity of information detected at a preceding time.

9. An image processing method comprising:
carrying out a compression processing of compressing image data, stored in a storage device, by using a compression parameter that is a value that specifies a data quantity after compression to generate compressed data;
detecting a quantity of information on an object contained in the compressed image data;
calculating a judgment value corresponding to the quantity of information;
carrying out a comparison processing of comparing the judgement value with a predetermined threshold; and
determining whether or not to update the compression parameter based on a result of the comparison processing,
wherein the image processing method further comprises:
assuming that transferable data quantity is a quantity of data transferable along a transmission path along which the image data is transmitted, updating the compression parameter by carrying out a generation processing including first computation of calculating a compression parameter for compressing the image data in such a way that a calculated data quantity relating to a data quantity of the compressed data is smaller than or equal to a first target data quantity specified based on the transferable data quantity;
carrying out compression processing on the image data by using the compression parameter for each of a plurality of unit areas of the image data; and
generating a plurality of compressed portions as the compressed data from the image data that is single image data,
wherein the storage device has a predetermined size storage capacity and successively stores the plurality of compressed portions, and
wherein the generation processing further includes second computation of calculating a compression parameter for compressing the image data in such a way that a maximum of data quantities of the plurality of compressed portions is smaller than or equal to a second target data quantity specified based on the storage capacity, and processing of comparing the compression parameter calculated by the first computation with the compression parameter calculated by the second computation and selecting a parameter that causes the data quantity after compression to decrease.

10. An endoscope system comprising:
an endoscope configured to capture an image of an object and to generate image data based on the image of the object;
an image data processing device comprising:
a processor configured to:
carry out a compression processing of compressing the image data, stored in a storage device, by using a compression parameter that is a value that specifies a data quantity after compression to generate compressed data;
detect a quantity of information on the object contained in the compressed image data;
calculate a judgment value corresponding to the quantity of information;
carry out a comparison processing of comparing the judgement value with a predetermined threshold; and
determine whether or not to update the compression parameter based on a result of the comparison processing,
wherein assuming that transferable data quantity is a quantity of data transferable along a transmission path along which the image data is transmitted, the processor is configured to update the compression parameter by carrying out a generation processing including first computation of calculating a compression parameter for compressing the image data in such a way that a calculated data quantity relating to a data quantity of the compressed data is smaller than or equal to a first target data quantity specified based on the transferable data quantity,
wherein the processor is configured to:
carry out compression processing on the image data by using the compression parameter for each of a plurality of unit areas of the image data; and
generate a plurality of compressed portions as the compressed data from the image data that is single image data,
wherein the storage device has a predetermined size storage capacity and successively stores the plurality of compressed portions, and
wherein the generation processing further includes second computation of calculating a compression parameter for compressing the image data in such a way that a maximum of data quantities of the plurality of compressed portions is smaller than or equal to a second target data quantity specified based on the storage capacity, and processing of comparing the compression parameter calculated by the first computation with the compression parameter calculated by the second computation and selecting a parameter that causes the data quantity after compression to decrease.

11. The endoscope system according to claim 10, wherein the endoscope system further comprises a video processor wirelessly connected to the processor, and is configured to decompress the compressed data to generate image data and to output the decompressed image data to a monitor.

12. The endoscope system according to claim 11, further comprising:
a first wireless communication circuit configured to transmit the compressed data; and
a second wireless communication circuit configured to receive the transmitted compressed data.

13. The endoscope system according to claim 12, wherein the image data processing device and the first wireless communication circuit is arranged within the endoscope, and
wherein the video processor is physically separate from the endoscope and is configured to decompress the compressed data received by the second wireless communication circuit.

14. The endoscope system according to claim 13, wherein the second wireless communication circuit is configured to transmit the compression parameter, and wherein the first wireless communication circuit is configured to receive the transmitted compressing parameter.

* * * * *